US012315629B2

(12) United States Patent
Butka et al.

(10) Patent No.: US 12,315,629 B2
(45) Date of Patent: May 27, 2025

(54) SYSTEMS AND METHODS FOR MANAGING PATIENT MEDICAL DEVICES

(71) Applicant: Murj, Inc., Santa Cruz, CA (US)

(72) Inventors: Richard T. Butka, Santa Cruz, CA (US); Christopher S. Irving, Santa Cruz, CA (US); Patrick Beaulieu, Santa Cruz, CA (US)

(73) Assignee: Murj, Inc., Santa Cruz, CA (US)

( * ) Notice: Subject to any disclaimer, the term of this patent is extended or adjusted under 35 U.S.C. 154(b) by 463 days.

(21) Appl. No.: 16/889,210

(22) Filed: Jun. 1, 2020

(65) Prior Publication Data

US 2020/0294663 A1 Sep. 17, 2020
US 2022/0375593 A9 Nov. 24, 2022

Related U.S. Application Data

(63) Continuation of application No. PCT/US2018/063670, filed on Dec. 3, 2018, which is
(Continued)

(51) Int. Cl.
*G16H 40/67* (2018.01)
*A61B 5/00* (2006.01)
*G16H 10/60* (2018.01)

(52) U.S. Cl.
CPC ........... *G16H 40/67* (2018.01); *A61B 5/0031* (2013.01); *A61B 5/742* (2013.01); *G16H 10/60* (2018.01)

(58) Field of Classification Search
CPC ........ G16H 10/60; G16H 15/00; G16H 40/63; G16H 40/67; G16H 40/40; G16H 80/00; G06Q 40/08
See application file for complete search history.

(56) References Cited

U.S. PATENT DOCUMENTS 4,173,971 A 11/1979 Karz
4,783,803 A 11/1988 Baker et al.
(Continued)

FOREIGN PATENT DOCUMENTS

JP 2001101306 A 4/2001
JP 2005063253 A 3/2005
(Continued)

OTHER PUBLICATIONS

Staudacher I, Nalpathamkalam AR, Uhlmann L, et al. Fully digital data processing during cardiovascular implantable electronic device follow-up in a high-volume tertiary center. Eur J Med Res. 2017;22(1):41. Published Oct. 11, 2017. doi:10.1186/s40001-017-0284-7 (Year: 2017).*
(Continued)

*Primary Examiner* — Joseph D Burgess
(74) *Attorney, Agent, or Firm* — Polsinelli PC

(57) ABSTRACT

Implementations described and claimed herein provide systems and methods for patient device management. In one implementation, interrogation data is received from a cardiac implantable electronic device corresponding to an interrogation for a patient. The interrogation data includes device data for the cardiac implantable electronic device and patient specific data for the patient. The interrogation data is normalized into manufacturer independent interrogation data. The manufacturer independent interrogation data is associated with a permitted user. A processing status is assigned to the interrogation using the manufacturer independent interrogation data. The interrogation is aggregated into a category based on the processing status, and the category is associated with an action by the permitted user.

20 Claims, 18 Drawing Sheets

Related U.S. Application Data a continuation-in-part of application No. 15/134,130, filed on Apr. 20, 2016, now Pat. No. 10,268,989.

(60) Provisional application No. 62/593,540, filed on Dec. 1, 2017, provisional application No. 62/149,960, filed on Apr. 20, 2015.

(56) References Cited

U.S. PATENT DOCUMENTS

| | | |
|---|---|---|
| 5,798,752 A | 8/1998 | Buxton et al. |
| D507,798 S | 7/2005 | Jewitt et al. |
| D571,818 S | 6/2008 | Loehr et al. |
| D579,020 S | 10/2008 | Aliaga |
| D606,088 S | 12/2009 | Yokouchi et al. |
| D617,808 S | 6/2010 | Thompson et al. |
| 7,761,507 B2 | 7/2010 | Herf et al. |
| 7,805,199 B2 | 9/2010 | KenKnight et al. |
| 8,060,821 B2 | 11/2011 | Seymour et al. |
| 8,112,151 B1 | 2/2012 | Cogan et al. |
| D694,259 S | 11/2013 | Klein |
| D695,758 S | 12/2013 | Tagliabue et al. |
| D703,688 S | 4/2014 | Choi |
| D731,520 S | 6/2015 | Xiong et al. |
| D732,051 S | 6/2015 | Jeong et al. |
| D741,882 S | 10/2015 | Shmilov et al. |
| D749,623 S | 2/2016 | Gray et al. |
| D753,670 S | 4/2016 | Tian |
| D757,065 S | 5/2016 | Jeon et al. |
| D761,842 S | 7/2016 | Johnson et al. |
| D763,879 S | 8/2016 | Worrell et al. |
| D764,501 S | 8/2016 | Dias et al. |
| D768,707 S | 10/2016 | Gagnier |
| D771,649 S | 11/2016 | Eze et al. |
| D777,177 S | 1/2017 | Chen et al. |
| D777,195 S | 1/2017 | Dain et al. |
| D779,514 S | 2/2017 | Baris et al. |
| D780,797 S | 3/2017 | Kisielius et al. |
| D781,889 S | 3/2017 | Wills et al. |
| D781,905 S | 3/2017 | Nakaguchi et al. |
| D782,526 S | 3/2017 | Rind et al. |
| D783,030 S | 4/2017 | Lee et al. |
| D785,022 S | 4/2017 | Vazquez et al. |
| D788,128 S | 5/2017 | Wada |
| D789,377 S | 6/2017 | Vazquez |
| D789,397 S | 6/2017 | Lee et al. |
| D789,982 S | 6/2017 | Christiana et al. |
| D792,424 S | 7/2017 | Meegan et al. |
| D792,426 S | 7/2017 | Theodore et al. |
| D794,047 S | 8/2017 | Gandhi et al. |
| D796,523 S | 9/2017 | Bhandari et al. |
| D798,320 S | 9/2017 | Gouvernel et al. |
| D800,741 S | 10/2017 | Rhodes |
| D803,845 S | 11/2017 | Arora |
| D805,525 S | 12/2017 | Dascola et al. |
| D806,097 S | 12/2017 | Rahn et al. |
| D807,379 S | 1/2018 | Pahwa et al. |
| D807,385 S | 1/2018 | Olsen et al. |
| D807,900 S | 1/2018 | Raji et al. |
| D807,911 S | 1/2018 | Zhou et al. |
| D808,399 S | 1/2018 | Derby et al. |
| D808,400 S | 1/2018 | Coren |
| D808,981 S | 1/2018 | Hazam et al. |
| D822,678 S | 7/2018 | Wu et al. |
| D823,326 S | 7/2018 | Pinzon Garcia et al. |
| D823,327 S | 7/2018 | Durkan et al. |
| D823,860 S | 7/2018 | Wiffen et al. |
| D829,229 S | 9/2018 | Durkan et al. |
| D830,382 S | 10/2018 | Marohn |
| D832,296 S | 10/2018 | Golden et al. |
| D833,459 S | 11/2018 | Blechschmidt et al. |
| D835,138 S | 12/2018 | Edgington, Jr. |
| D840,426 S | 2/2019 | Dieken et al. |
| D841,017 S | 2/2019 | Bathla |
| D841,675 S | 2/2019 | Hoffman et al. |
| D843,403 S | 3/2019 | Casse et al. |
| D845,973 S | 4/2019 | Jaycobs |
| D845,974 S | 4/2019 | Cooperman et al. |
| D847,165 S | 4/2019 | Kolbenheyer |
| D849,014 S | 5/2019 | Senders |
| D849,029 S | 5/2019 | Cooperman et al. |
| D849,773 S | 5/2019 | Jiang et al. |
| 10,289,660 B2 | 5/2019 | Karunamuni et al. |
| D853,412 S | 7/2019 | Hofner et al. |
| D853,420 S | 7/2019 | Ambrose et al. |
| D854,030 S | 7/2019 | Dascola et al. |
| D854,565 S | 7/2019 | McLaughlin et al. |
| D860,237 S | 9/2019 | Li et al. |
| D860,239 S | 9/2019 | Lirov et al. |
| D867,389 S | 11/2019 | Jamison et al. |
| D869,488 S | 12/2019 | Storr |
| D870,762 S | 12/2019 | Mendoza Corominas et al. |
| D872,117 S | 1/2020 | Kobayashi et al. |
| D874,486 S | 2/2020 | Ragland et al. |
| D875,747 S | 2/2020 | Iida et al. |
| D875,761 S | 2/2020 | Heffernan et al. |
| D876,454 S | 2/2020 | Knowles et al. |
| D877,167 S | 3/2020 | Knowles et al. |
| D879,112 S | 3/2020 | Hejazi et al. |
| D879,134 S | 3/2020 | Jones |
| D880,513 S | 4/2020 | Wang et al. |
| D881,908 S | 4/2020 | Sunil et al. |
| D881,910 S | 4/2020 | Lin |
| D888,739 S | 6/2020 | Christiana et al. |
| D898,056 S | 10/2020 | Olson |
| D905,734 S | 12/2020 | Christiana et al. |
| D906,358 S | 12/2020 | Christiana et al. |
| D914,040 S | 3/2021 | Butka et al. |
| D924,258 S | 7/2021 | Klimer et al. |
| D949,898 S | 4/2022 | Olson |
| 11,456,072 B1 | 9/2022 | Irving et al. |
| 2001/0039504 A1 | 11/2001 | Linberg et al. |
| 2001/0051765 A1 | 12/2001 | Walker et al. |
| 2002/0056575 A1 | 5/2002 | Keely et al. |
| 2002/0082665 A1* | 6/2002 | Haller ............... A61N 1/37264 607/60 |
| 2002/0089547 A1 | 7/2002 | Huapaya |
| 2004/0008224 A1 | 1/2004 | Molander et al. |
| 2004/0071344 A1 | 4/2004 | Lui et al. |
| 2005/0021370 A1 | 1/2005 | Riff et al. |
| 2005/0065445 A1 | 3/2005 | Arzbaecher et al. |
| 2005/0192649 A1* | 9/2005 | Shehadeh .......... A61N 1/37211 607/60 |
| 2005/0278140 A1 | 12/2005 | Wang |
| 2007/0016857 A1 | 1/2007 | Polleck et al. |
| 2007/0060797 A1 | 3/2007 | Ball et al. |
| 2007/0135855 A1 | 6/2007 | Foshee et al. |
| 2008/0007570 A1 | 1/2008 | Wessel et al. |
| 2008/0109051 A1 | 5/2008 | Splinter et al. |
| 2009/0062671 A1 | 3/2009 | Brockway et al. |
| 2009/0187426 A1 | 7/2009 | Kerstna et al. |
| 2010/0005411 A1 | 1/2010 | Duncker et al. |
| 2010/0114993 A1 | 5/2010 | Holschbach et al. |
| 2010/0134353 A1 | 6/2010 | Van Diggelen |
| 2011/0004277 A1* | 1/2011 | Johnson ............... G16H 40/67 607/60 |
| 2011/0054264 A1 | 3/2011 | Fischell et al. |
| 2011/0106669 A1 | 5/2011 | Baghdassarian |
| 2011/0119212 A1 | 5/2011 | De Bruin et al. |
| 2012/0095300 A1 | 4/2012 | McNair |
| 2012/0141964 A1 | 6/2012 | Lee |
| 2012/0143017 A1 | 6/2012 | Snyder |
| 2012/0194558 A1 | 8/2012 | Dykes et al. |
| 2012/0223889 A1 | 9/2012 | Medlock et al. |
| 2012/0288881 A1 | 11/2012 | Liu |
| 2012/0290599 A1 | 11/2012 | Tian et al. |
| 2013/0035209 A1 | 2/2013 | Gilley et al. |
| 2013/0124186 A1 | 5/2013 | Donabedian et al. |
| 2013/0232437 A1 | 9/2013 | Kim |
| 2013/0274705 A1 | 10/2013 | Burnes et al. |
| 2013/0317852 A1* | 11/2013 | Worrell ................ G16H 40/63 705/2 |
| 2015/0227691 A1 | 8/2015 | Bhattacharya et al. |
| 2015/0295914 A1 | 10/2015 | Kelishadi |

(56) References Cited

U.S. PATENT DOCUMENTS

| | | | |
|---|---|---|---|
| 2015/0324549 A1* | 11/2015 | Nearhood | G16H 15/00 |
| | | | 705/2 |
| 2015/0370920 A1 | 12/2015 | Van Os et al. | |
| 2016/0246931 A1 | 8/2016 | Rajan et al. | |
| 2016/0292456 A1 | 10/2016 | Dubey et al. | |
| 2016/0306929 A1 | 10/2016 | Butka et al. | |
| 2017/0262605 A1* | 9/2017 | Wadhwa | G16H 10/60 |
| 2017/0312534 A1 | 11/2017 | Cao et al. | |
| 2019/0026838 A1 | 1/2019 | Tan et al. | |
| 2019/0083030 A1 | 3/2019 | Thakur et al. | |
| 2019/0109757 A1 | 4/2019 | Oliveira et al. | |
| 2019/0213544 A1 | 7/2019 | Spirig et al. | |
| 2022/0144427 A1 | 5/2022 | Vernon et al. | |
| 2022/0280047 A1 | 9/2022 | Stadler et al. | |
| 2022/0296906 A1 | 9/2022 | Westphal et al. | |

FOREIGN PATENT DOCUMENTS

| | | | |
|---|---|---|---|
| JP | 2005319151 A | 11/2005 | |
| JP | 2021506039 A | 2/2021 | |
| WO | 2010051175 A1 | 5/2010 | |

OTHER PUBLICATIONS

T. Tran, H.-S. Kim and H. Cho, "A Development of Ubiquitous Biomedical Interface for Facilitating Medical Device Connectivity," 7th IEEE International Conference on Computer and Information Technology (CIT 2007), Aizu-Wakamatsu, Japan, 2007, pp. 1094-1099, doi: 10.1109/CIT.2007.58 (Year: 2007).*

E. T. van der Velde, H. Foeken, T. Witteman, L. van Erven and M. J. Schalij, "Integration of remote monitoring data into the hospital electronic health record system: Implementation based on international standards," 2011 Computing in Cardiology, Hangzhou, China, 2011, pp. 581-584 (Year: 2011).*

Dec. 27, 2022—(US) Non-Final Office Action—U.S. Appl. No. 17/809,509, 24 pages.

ANGI71., "Vector Buttons Blue and White," May 17, 2008, Retrieved from the Internet: URL: https://www.istockphoto.com/vector/vector-buttons-blue-and-white-gray-gm95492721-6143274, 5 pages.

E. T. van der Velde, H. Foeken, T. Witteman, L. van Erven and M. J. Schalij, "Integration of remote monitoring data Into the hospital electronic health record system: Implementation based on international standards," 2011 Computing In Cardiology, 2011, pp. 581-584 (Year: 2011).

International Search Report and Written Opinion, PCT/US2016/028470, dated Jul. 22, 2016, 10 pages.

International Search Report and Written Opinion-PCT/US2022/073231, Sep. 27, 2022, 9 pgs.

JP Office Action, JP2020-548891_Aug. 31, 2021.

Notice of Allowance for U.S Appl. No. 15/134,130, mailed on Feb. 21, 2019, 8 pages.

Notice of Allowance for U.S. Appl. No. 17/654,949, mailed on May 9, 2022, 8 pages.

Notice of Allowance for U.S. Appl. No. 17/654,949, mailed on May 23, 2022, 2 pages.

Notice of Allowance for U.S. Appl. No. 29/643,240, mailed on Aug. 10, 2020, 7 pages.

Notice of Allowance for U.S. Appl. No. 29/643,241, mailed on Aug. 12, 2020, 8 pages.

Notice of Allowance for U.S. Appl. No. 29/643,242, mailed on May 22, 2020, 7 pages.

Notice of Allowance for U.S. Appl. No. 29/643,244, mailed on Aug. 10, 2020, 7 pages.

Notice of Allowance for U.S. Appl. No. 29/763,698, mailed on Jun. 8, 2022, 6 pages.

Notice of Allowance for U.S. Appl. No. 29/764,234, mailed on Jul. 8, 2022, 7 pages.

Office Action for U.S Appl. No. 15/134,130, mailed on May 9, 2018, 18 pages.

Office Action for U.S. Appl. No. 17/809,509, mailed on Apr. 17, 2023, 19 pages.

Office Action for U.S Appl. No. 29/763,144, mailed on Oct. 21, 2022, 6 pages.

Office Action for U.S. Appl. No. 29/763,698, mailed on Sep. 7, 2021, 6 pages.

Office Action for U.S. Appl. No. 29/764,234, mailed on Sep. 7, 2021, 7 pages.

Shlain A., "Common Icon Set," Apr. 26, 2015, Retrieved from the Internet: URL: https://www.iconfinder.com/iconsets/common-3, 1 Page.

Stackexchange "Dynamic Progress Indicator," Mar. 25, 2014, Retrieved from the Internet: URL: https://ux.stackexchange.com/questions/54570/dynamic-progress-indicator, 2 pages.

Jul. 31, 2023—(US) Final Office Action—U.S. Appl. No. 29/763,144, 25 Pages.

Jul. 2, 2024—(JP) Office Action—App 2023-580815, 5 Pages.

May 10, 2024—(US) Notice of Allowance—U.S Appl. No. 29/856,161, 29 Pages.

May 29, 2024—(US) Final Office Action—U.S Appl. No. 29/763,144, 13 Pages.

"Envelope 2 Icon" Jul. 7, 2017, posted atxxx.com, [site visited Apr. 29, 2024], https://web.archive.Org/web/20170707063016/https://www.iconexperience.com/i_collection/icons/?icon=envelope2 (Year: 2017).

Taylor, Nick Paul, "Murj scoops $8.5M to enable boom in devices and data" May 9, 2018, posted at fiercebiotech.com, [site visited Apr. 29, 2024], https://www.fiercebiotech.com/medtech/murj-scoops-8-5m-to-enable-boom-devices-and-data (Year: 2018).

* cited by examiner

SYSTEMS AND METHODS FOR MANAGING PATIENT MEDICAL DEVICES

CROSS-REFERENCE TO RELATED APPLICATIONS

The present application is a continuation under 35 U.S.C. 111 (a) of Patent Cooperation Treaty No. PCT/US2018/063670, entitled "Systems and Methods for Managing Patient Medical Devices" and filed on Dec. 3, 2018, which claims benefit under 35 U.S.C. § 119 to U.S. Provisional Patent Application No. 62/593,540, entitled "Systems and Methods for Managing Patient Medical Devices" and filed on Dec. 1, 2017. PCT/US2018/063670 is also a continuation-in-part of U.S. application Ser. No. 15/134,130, entitled "Medical Device Platform" and filed on Apr. 20, 2016, now U.S. Pat. No. 10,268,989, which claims benefit under 35 U.S.C. § 119 to U.S. Provisional Patent Application No. 62/149,960, entitled "Medical Device Platform" and filed on Apr. 20, 2015. Each of these applications is specifically incorporated by reference herein in its entirety.

TECHNICAL FIELD

Aspects of the present disclosure relate to managing patient medical devices for one or more patients and more particularly to systems and methods for managing one or more cardiac implantable electronic devices.

BACKGROUND

Implantable medical devices are regularly used to treat and/or monitor a variety of medical conditions. For example, cardiac implantable electronic devices (CIED), such as implantable cardioverter defibrillators (ICDs) are often utilized to regulate and monitor cardiac functions. CEIDs may include, without limitation: pacemarkers (PMs), which prevent slow heart rates using low-energy electrical pulses; implantable cardioverter defibrillators (ICDs), which are used to detect abnormal heart arrhythmias and deliver lifesaving shocks to prevent sudden cardiac arrest; implantable loop recorders (ILRs) and implantable cardiac monitors (ICMs), which continuously monitor cardiac data and transmit data to the clinic as prescribed by a clinician and at the patient's discretion; and the like. Such CIEDs store and may periodically transmit information relating to the operation of the device outside the body for analysis, programming, and/or the like. More particularly, CIEDs store and transmit information for in-office or remote monitoring by a medical provider.

However, medical providers are often responsible for a large number of patients having a range of devices manufactured by disparate manufacturers. Each of the manufacturers typically uses a unique proprietary data format for the information communicated from its device, as well as for any data provided to the medical provider that summarizes this information. With the medical provider receiving information in a range of unique formats, it is challenging for the medical provider to efficiently manage the care of the patients across various device types and manufacturers. These challenges are exacerbated by the information typically being presented to the medical provider for review and analysis in the order in which the transmissions are received. Accordingly, the medical provider cannot determine whether any of the transmissions may necessitate more urgent review. Further, reviewing the information associated with a transmission is often onerous, which wastes resources, particularly on transmissions that are not clinically relevant.

It is with these observations in mind, among others, that various aspects of the present disclosure were conceived and developed.

SUMMARY

Implementations described and claimed herein address the foregoing problems by providing systems and methods for patient device management. In one implementation, interrogation data is received from a cardiac implantable electronic device corresponding to an interrogation for a patient. The interrogation data includes device data for the cardiac implantable electronic device and patient specific data for the patient. The interrogation data is normalized into manufacturer independent interrogation data. The manufacturer independent interrogation data is associated with a permitted user. A processing status is assigned to the interrogation using the manufacturer independent interrogation data. The interrogation is aggregated into a category based on the processing status, and the category is associated with an action by the permitted user.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Figure 1:
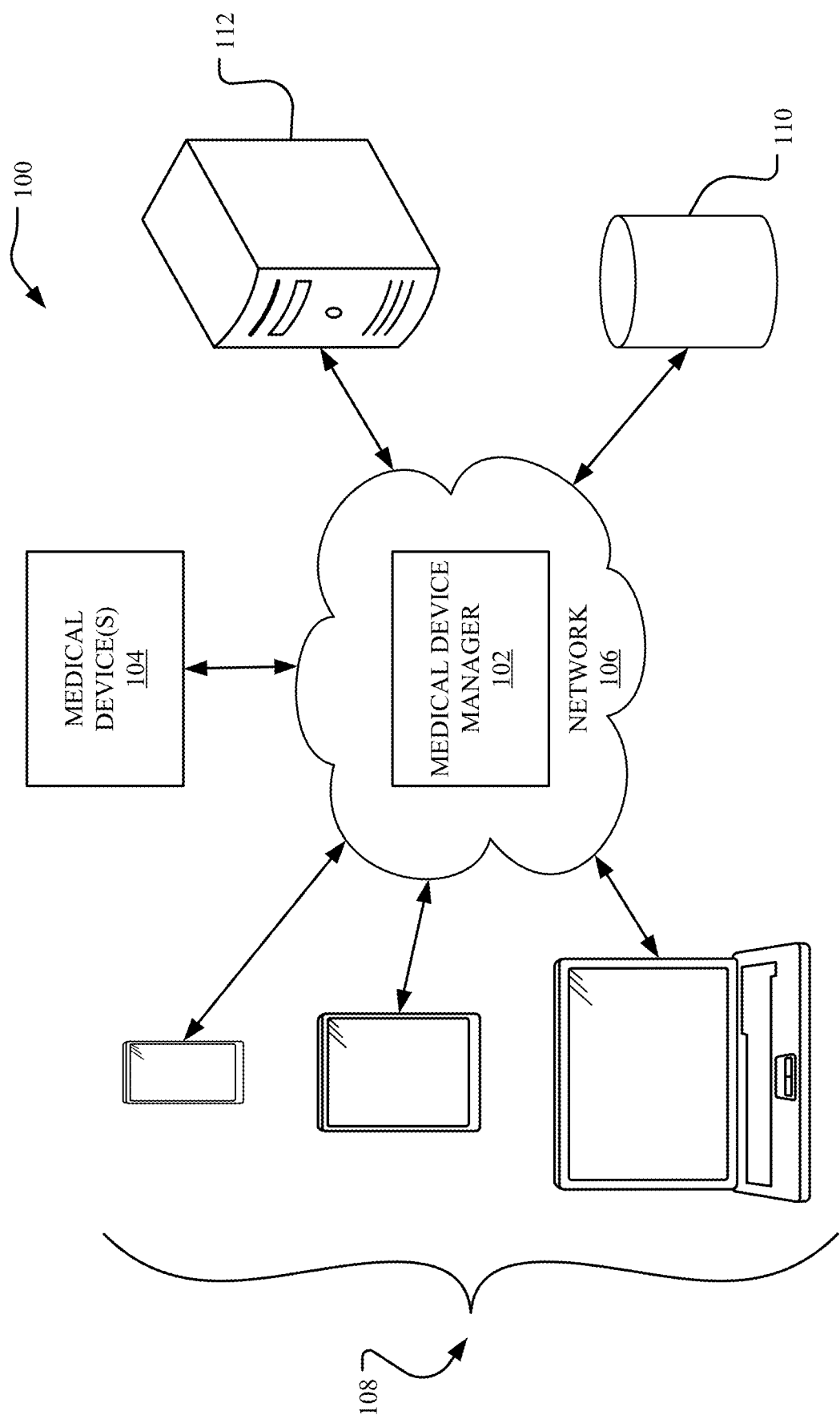
FIG. 1 illustrates an example network environment, including a medical device manager running on a server or other computing device coupled with a network, for managing one or more cardiac implantable electronic devices.

Aspects of the present disclosure involve systems, methods, computer program products, and the like for a medical device management platform for managing one or more implantable or otherwise wearable electronic devices. The electronic devices, may include medical devices, such as one or more cardiac implantable electronic devices (CIEDs). The platform may, in general, receive operational transmissions from one or more medical devices, such as CIEDs, of patients to manage the care of those patients, including receipt of data, reports, and information from such devices to enable a provider to view, document, report on, and generate a care strategy for the patients. Such operation transmissions may be received at the management platform through many sources, including the corresponding device, a device programming machine, reporting from the patient or a manufacturer, or from a third-party entity receiving the transmissions from the device. The transmissions provide general operational information of the corresponding device and may, in some instances, include alerts or events on the device operation, as well as packaged reports defined by the device manufacturer. These alerts or events may trigger some form of patient care as it pertains to the operation of the device and the health of the device patient.

The management platform may also provide one or more interfaces through which medical personnel or other users of the platform may manage the receipt of the device transmissions. For example, the management platform may provide the one or more interfaces to a user computing device through which the user may review transmissions, establish one or more workflows or medical plans in response to the transmission, alert a patient to a device condition, and/or share device information with other medical personnel. Each manufacturer of CEIDs has unique in-office programmers and unique remote data access portals to enable monitoring of the corresponding CEIDs. As such, clinics are faced with accessing and reviewing CEID data to create patient reports using a myriad of data sources, including, for example, a programmer and a data portal for each manufacturer.

In one particular implementation, the transmission management interface may allow a clinic technician to access the interface and receive a listing of received device transmissions. The interface may further provide for generating of one or more reports (e.g., dockets) or workflows associated with the received transmissions to process the transmissions to completion. Such dockets may include medical plans for a patient in response to the transmission to treat the patient based on the device information. Statistics and other measurements of the received transmissions and resulting care protocols may also be provided through the interface tool to improve the operation and efficiency of a clinic, or to improve care to the patient, or to share data with another entity with access to the interface. In this manner, management of device transmissions is simplified and improved for users of the device management platform interface.

Reference is now made to FIG. 1 which illustrates an example network environment 100, including a medical device manager 102 running on a server 112 or other computing device coupled with a network 106, for managing one or more cardiac implantable electronic devices 104. In one implementation, a user, such as a member of a medical team and/or a third party to which access is delegated to manage or complete management services, accesses and interacts with a medical device manager portal 102 using a user device 108 to access or manage one or more medical devices via a network 106 (e.g., the Internet). The user device 108 is generally any form of computing device capable of interacting with the network 106, such as a personal computer, terminal, workstation, portable computer, mobile device, smartphone, tablet, multimedia console, etc. The network 106 is used by one or more computing or data storage devices (e.g., one or more databases 110 or other computing units described herein) for implementing the medical device manager 102 and other services, applications, or modules in the network environment 100.

In one implementation, the network environment 100 includes at least one server 112 hosting a website or an application that the user may visit to access the medical device manager 102 and/or other network components, including device programming machine that reside in a physician office and are utilized when in the presence of a patient. The server 112 may be a single server, a plurality of servers with each such server being a physical server or a virtual machine, or a collection of both physical servers and virtual machines. In another implementation, a cloud hosts one or more components of the network environment 100. The user devices 108, the server 112, and other resources connected to the network 106 may access one or more other servers to access to one or more websites, applications, web services interfaces, storage devices, computing devices, or the like that are used for integrated healthcare delivery. The server 112 may also host a search engine that the medical device manager 102 uses for accessing, searching for, and modifying patient data, team member data, education data, and other data. In one implementation, the medical device manager 102 provides access to data and/or other information of one or more implantable medical devices 104.

CEID monitoring by a professional typically occurs over the life of a patient. Such monitoring is subject to reimbursement and care guidelines. Typically, CEID care involves four remote data checks per year for patients having a PM or ICD, at least one in-office check per year for PM or ICD patients, and eleven remote data checks per year for ICM or ILR patients. Healthcare insurance in the U.S. is generally consistent with these guidelines. However, while healthcare insurance reimbursements exist, they often do not cover the labor expense involved in retrieving, reviewing, and documenting device transmissions. With the rapid adoption of new ILRs and ICMs and the increasing volume of data, the estimated transmission burden of these guidelines could exceed 800 million CEID transmissions over the next five years. Compliance with these guidelines improves patient outcomes and lowers healthcare system costs, reducing mortality by nearly 2.5 times for patients with PMs and reducing hospitalizations by over 65% in ICD patients. However, due to the burdens involved with these guidelines, it is estimated that less than 30% of patients are monitored in accordance with these guidelines.

As such, medical devices 104 may be in communication with network 106 to provide operational data to the medical device manager 102. For example and as described above, cardiac implantable electronic devices (CIED), such as implantable cardioverter defibrillators (ICDs) and the like, often transmit information relating to the operation of the device outside the body for analysis, programming, and/or the like. In some cases, a clinic retrieves data for the medical devices 104 from a device manufacturer secure website and/or from device programming machines physically located in a provider office. The data generated by the medical devices 104 is typically reviewed by a provider. A typical provider implants and monitors transmissions from the full range of manufacturers and device models and types. Providers rarely implant and monitor a single devices type. In terms of data transmissions and modalities of review of data transmissions, each of the manufacturers uses unique and proprietary data formats, displays, access protocols, reports, and programming machines. With the medical provider receiving data in this wide range of unique and disparate formats, it is challenging for the medical provider to efficiently manage the care of patients. The burdens of data access and management are a major impediment to better patient care. Cumbersome workflow creates excessive costs, impedes adoption of remote care, which is a superior care modality, leads to missed reimbursement opportunities, and forces some clinics to abandon remote care and instead push patients to the lower volume of in-office care, which leads to even further care reduction due to low patient compliance and greater healthcare system burdens associated with increased hospitalization. As such, as described in more detail below, the medical device manager 102 thus allows a user to manage, analyze, and/or store data from the one or more medical devices 104 across various device types and disparate manufacturers.

Figure 2:
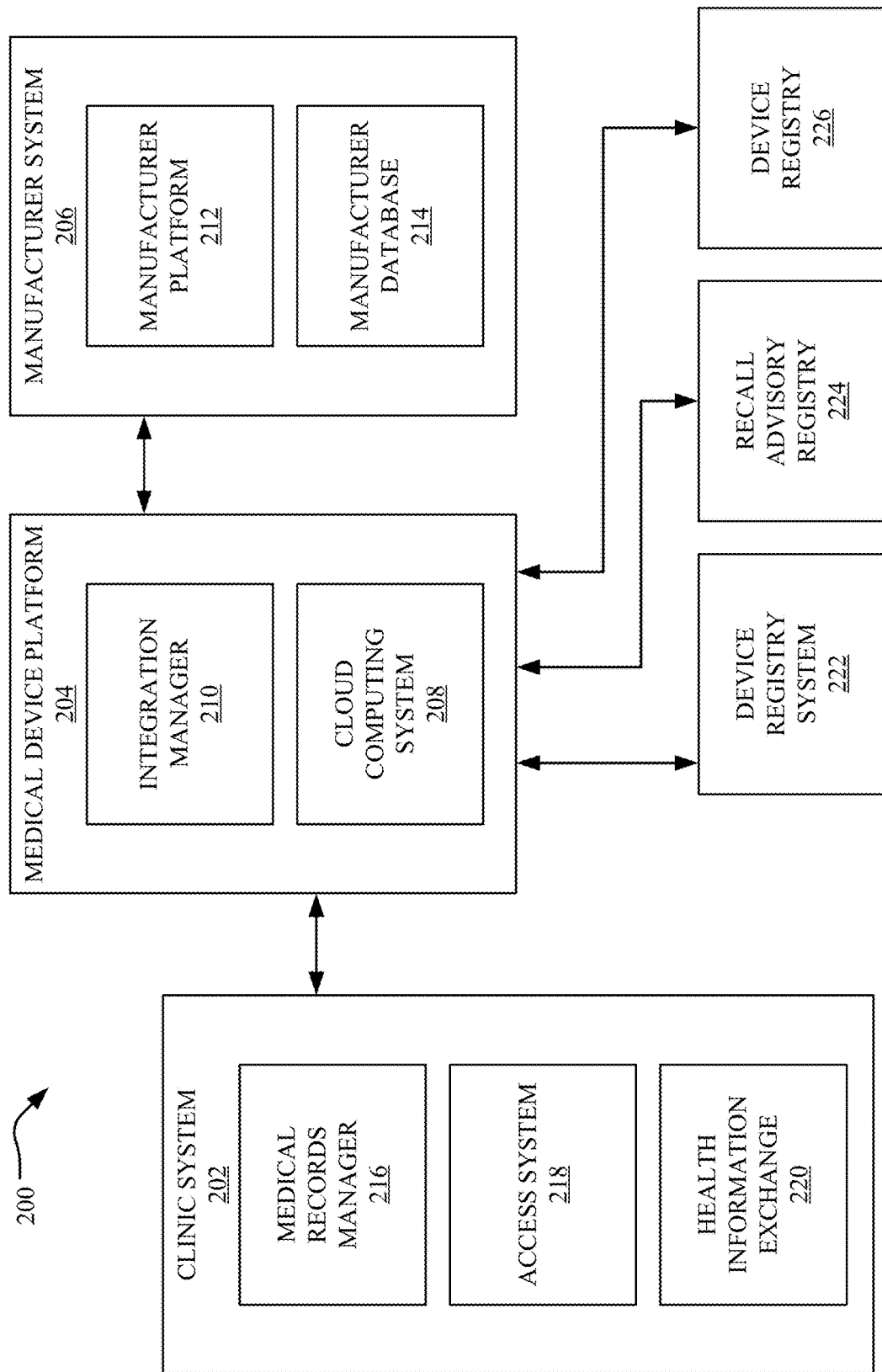
FIG. 2 is a block diagram of a medical device data communication system including an example medical device data platform.

Turning to FIG. 2, the medical device manager 102 may include a medical device data communication system 200. In one implementation, the medical device data communication system 200 includes a medical device platform 204 in communication with multiple implantable medical device manufacturer systems 206 and multiple clinic systems 202. The medical device platform 204 may be communicatively coupled with the manufacturer systems 206 and the clinic systems 202 via a wide area network (WAN), such as, for example, the Internet. In some implementations, each of the manufacturer systems 206 may be associated with a unique implantable medical device manufacturer. In other examples, each of the manufacturer systems 206 may be associated with a unique pairing of an implantable medical device manufacturer and a particular medical clinic or office. In the example of the system 200 of FIG. 2, the manufacturer system 206 may include a manufacturer platform 212, such as, for example, a web server, that retrieves from a device database 214 diagnostic and related data previously uploaded from a plurality of implantable medical devices. Such data may have been retrieved previously from the various implantable medical devices by way of a clinic or office, or by way of a remote monitor, as described above.

The medical device platform 204, as depicted in FIG. 2, may include an integration manager 210 that accesses the diagnostic and related data for the implantable medical devices from each of the manufacturer systems 206. In an example, the integration manager 210 may provide a clinical information system (CIS) identifier associated with a particular clinic to the manufacturer platform 206 to retrieve the diagnostic data and related information, which may be in the form of Implantable Device Cardiac Observation (IDCO) messages. In some implementations, messages between the integration manager 210 and the manufacturer platform 212 may be in the form of alternative, enhanced, or augmented data messages. For example, IDCO messages often contain information formatted as summary reports in Portable Document Format (PDF). In other examples, IDCO-like messages may provide more detailed or "raw" data, such as numerical and/or graphical electrogram (EGM) data regarding arrhythmia or other cardiac episodes detected by the implantable device in integer, floating-point, or another data format. Such information may facilitate easier and/or more detailed processing of the device data within the medical device platform 204.

The integration manager 210 may then process the retrieved information to generate patient-oriented information and/or provider-oriented information. In some examples, the retrieved information from the various implantable medical devices may be processed into a format that is unified or generalized across all manufacturers and/or devices of a particular type. The integration manager 210 may then forward the processed information to a cloud computing system 208 that may provide one or more web portals for the clinic systems 202 as well as individual patient communication systems not depicted in FIG. 2. In other examples, the integration manager 210 may forward the retrieved device data to the cloud computing system 208, which may then operate as an information processor to process the data. The cloud computing system 208 may also generate and provide analytics and other advanced information based on the processed information via the web portals. Examples of web portals and the generating and providing of analytics of the information are described in more detail below. The cloud computing system 208, in some examples, may include multiple computer devices or systems configured to perform the various operations ascribed herein to the cloud computing system 208.

As illustrated in FIG. 2, a user (e.g., one or more doctors, nurses, technicians, analysts, etc.) may employ a clinic system 202 to retrieve the processed device information, possibly including the analytics and other advanced information of one or more implantable medical devices. In some examples, the clinic system 202 may include a clinic access system 218 (e.g., a desktop computer, a laptop computer, a tablet computer, a smart phone, etc.) from which the user may access a web portal provided by the cloud computing system 208 to retrieve provider-oriented information, such as the medical device manager 102. As shown in FIG. 2, the clinic system 202 may also include one or more of an electronic medical records manager system 216 configured to store and facilitate access to medical records of the patients of the clinic, and a health information exchange (HIE) system 220 configured to exchange health and medical information for the patients of the clinic with other computing systems external to the clinic system 202. In one implementation, a user may sign on or log on to the cloud computing system 208, the medical recorder manager 216, and/or the HIE system 220 using a single sign-on (SSO) procedure, thus reducing the amount of time normally required by the user to access each of these systems individually.

In some examples, the integration manager 210 may retrieve the device diagnostic data and other device information via a communication connection with one or more of the implantable medical devices, thus possibly reducing the need for one or more of the manufacturer systems 206. In those examples and others, the integration manager 210 and/or the cloud computing system 208 may forward or "push" the unprocessed and/or processed device information, as well as the analytics and other advanced information to one or more of the manufacturer systems 206 for use by the corresponding manufacturers of the devices.

As depicted in FIG. 2, the cloud computing system 208 may also communicate with, retrieve data from, and/or transmit data to, other systems external to the medical device platform 204. For example, the cloud computing system 208 may access a medical device registry system 222 to supply data regarding the efficacy and/or safety of, patient response to, and other information regarding the use of, the various implantable medical devices. The cloud computing system 208 may also access the device registry data to correlate that data with the processed information received from the various implantable medical devices associated with the cloud computing system 208.

The cloud computing system 208 may also access registry information and device data system 226 configured to track accurately each of the implantable medical devices associated with the cloud computing system 208. For example, the cloud computing system 208 may employ data obtained from the registry information and device data system 226 to correlate or associate accurately the information associated with one or more of the implantable medical devices that is processed within the cloud computing system 208 with the data retrieved from the medical device registry system 222.

In some examples, the cloud computing system 208 may access a recall advisory registry database 224 to retrieve product recall data for an array of implantable medical devices, including those devices associated with the medical device platform 204. Further, the cloud computing system 208 may inform a user via the clinic system 202 and/or via web portal of any recalls involving their corresponding implantable medical devices in a timely manner. Such data may be pushed to the user via the web portal, email, text, or other communication means. In one example, the medical device platform 204 includes the recall advisory registry database 224, and may populate the recall advisory registry database with data from a variety of sources, such as, for example, official federal governing bodies, state or national medical boards, news agencies, and so forth.

Figure 3:
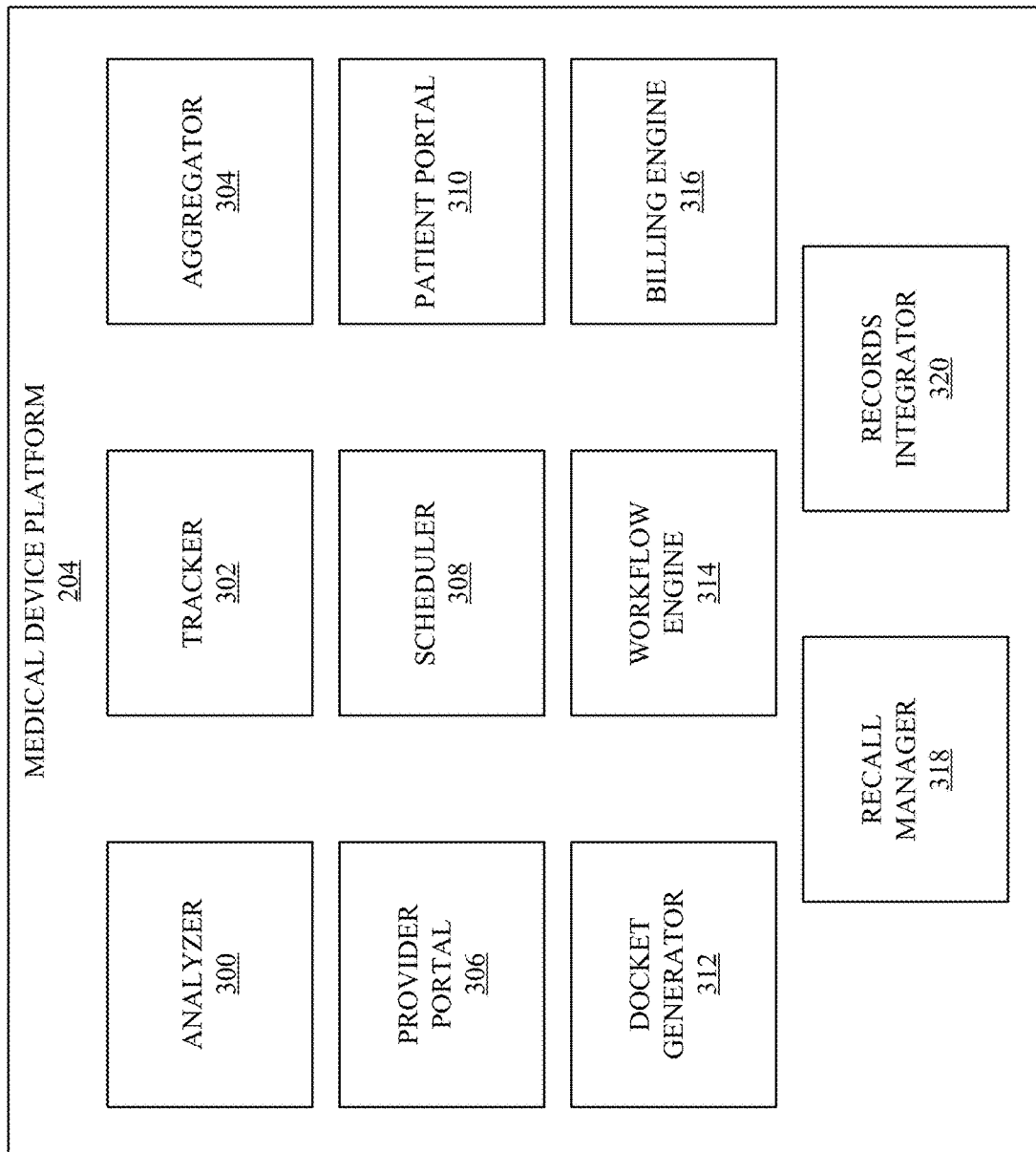
FIG. 3 is a block diagram of the example medical device data platform.

FIG. 3 is a block diagram of an example of the medical device platform 204 of FIG. 2. As depicted in FIG. 3, the medical device platform 204 may include one or more of an analyzer module 300, tracker module 302, an aggregator module 304, a provider portal module 306, a schedule module 308, a patient portal 310, a docket generator module 312, a workflow engine 314, a billing engine 316, a recall manager 318, and/or a records integrator 320. Other modules not specifically described herein may also be included in the medical device platform 204 in other examples. Further, each of these modules may be incorporated within the integration manager 210 and/or the cloud computing system 208, as depicted in FIG. 2.

The analyzer module 300 may be configured to analyze information and data received from one or more CIEDs and provide automated snapshots of trends of the analyzed information. In some implementations, such information may be analyzed for a particular clinic or for multiple clinics. As described above, the one or more CIEDs may transmit stored or obtained information or data on the performance or operation of the implanted device. This information is transmitted or downloaded to the medical device platform 204 and analyzed by the analyzer module 300. The analysis of the information may provide particular snapshots of analyzed and/or aggregated information through a portal (described in more detail below). For example, the analyzer module 300 may provide information based on the type of device associated with the information or data, a manufacturer of the device, or a particular device model. Similarly, a tracker module 302 may be included in the medical device platform 204 for tracking trends in the received data over time. Through the combination of the analyzer module 300, the tracker module 302, and other modules, snapshots of device information may be provided, such as trends in CIED patient growth, percentage of data received sorted by manufacturer, overall transmissions of data received, device counts applied to a standard of care normalization, and the like. More analytics and information concerning the received data from the one or more medical devices and analyzed by the analyzer module 300 are discussed in more detail below.

An aggregator module 304 may also be included in the medical device platform 204. In general, the aggregator module 304 may be configured to retrieve the diagnostic and other device-related data from each of the manufacturer systems 206 discussed above and/or information from one or CIEDs. In an example, the aggregator module 304 may utilize manufacturer-specific courier engines to retrieve the data using the particular security measures, communication protocols, data formats, and other characteristics of the specific manufacturer system 206 required to retrieve the data therefrom. Moreover, each of the manufacturer-specific courier engines may convert the retrieved data into a unified format that is applied to the data received from all of the manufacturer systems 206 so that the cloud computing system 208 may process the device data to yield patient-oriented information and/or provider-oriented information in a consistent manner. In at least some examples, the use of the aggregation module 304 may reduce the need for in-clinic information technology (IT) specialists to retrieve the diagnostic data and other information from the implantable medical devices, especially for devices from multiple manufacturers, each of which may employ their own data formats, communication protocols, and the like.

The provider portal 306 may be configured to present a web interface to the clinic systems 202 that facilitates access by clinic staff to the provider-oriented device data information corresponding to the patients of that clinic. Similarly, the medical device patient portal 310 may be configured to provide a separate web interface to the patients of a particular clinic, or to the patients of implantable medical devices in general. The provider portal 306 and the patient portal 310 may utilize a log on of the clinic staff and the patient, respectively, to allow access to the provider-oriented or patient-oriented information, as appropriate. In some examples, logging on to provider portal 306 may facilitate access by clinic staff to other systems external to or located within the clinic system 202 (e.g. the medical records manager 216 and/or the HIE system 220 of FIG. 2) via single sign-on (SSO) functionality, as mentioned above. In addition, the provider portal 306 and/or the patient portal 310 may provide an application programming interface (API) that facilitates patient or provider access to electronic health records (EHRs) of the patient that may contain access points, such as, for example, embedded web links, to the device-related information.

In other examples, the medical device platform 204 may provide or include other information portals aside from the provider portal 306 and the patient portal 310, such as, portals for administrative personnel associated with a clinic or insurance company, executives associated with a clinic or insurance company, employees of one or more cardiac device manufacturers, and so on. In such examples, each particular class or group of potential users of the medical device platform 204 may be associated with a particular access scope or set of access rights, set of security requirements (e.g., requirements for user names, passwords, computer systems, etc.). As a result, each group of users may employ a corresponding user portal similar to the provider portal 306 and/or the patient portal 310. Each particular portal may be accessible by way of different Uniform Resource Locators (URLs), or may be distinguished in one or more other ways.

The scheduling module 308 may be configured to present a web interface (e.g., the web portals described above, or a separate web portal) accessible to patients and/or clinic staff to schedule appointments, such as in-office or in-home device check or programming visits, with clinic patients. In some examples, the scheduling web portal may be customized for each particular clinic, possibly providing additional information regarding services rendered by the clinic, descriptions of the members of the clinic staff, and so on.

The docket generator module 312 may be configured to create one or more dockets associated with a patient or a collection of received data. In general, the docket is a report of sorts that summarizes or otherwise provides interpretations and records of received patient CIED transmissions. All or portions of the docket may be populated with information received during transmissions and provided to clinic staff for analysis and approval. The docket may include such information as device manufacturer information, clinic staff approval, clinical data, care plans, audit trails for the device, patient information, summary statements of data analysis, and the like. Any information concerning the patient information or information received from multiple medical devices may be included in the docket through the docket generator module 312.

The workflow engine 314 may be configured to monitor information regarding periodic device checks, the resulting diagnostic data, and other information related to the implantable medical devices of one or more patients, and based on that information, recommend changes to the workflow of the clinic, such as, for example, changes to device check schedules, changes to the particular types of information retrieved from the implantable medical device, changes to how the retrieved information is processed, and the like, thus possibly rendering the operations of the clinic more efficient.

The billing engine 316 may be configured to present an interface (e.g., via the provider-oriented web portal) through which clinical staff may enter an indication of one or more clinical actions taken with respect to an implantable medical device of a patient, and in which a currently appropriate billing code representing that action is generated. Further, the resulting billing codes for one or more such actions may further be inserted into a billing code summary sheet or other format for presentation to the patient, medical insurance company, and so on. In some examples, the billing engine 316 may receive or retrieve information regarding changes in billing codes from the Centers for Medicare and Medicaid Services (CMS) employable in a prospective payment system (PPS) and utilize those changes to update the billing codes corresponding to clinical actions related to implantable medical devices.

The device recall management module 318 may be configured to provide (e.g., "push") timely notifications and more detailed information to clinic staff or other users regarding recalls of implantable medical devices associated with that clinic. As mentioned above, the medical device recall management module 318 may collect information from one or more sites, such as, for example, official federal governing bodies, state and/or national medical boards, news agencies, and so on, and generate recall information, collect such information in the recall advisory registry database 224, and provide notifications regarding discovered recalls of implantable medical devices based on the information in the recall advisory registry database by way of, for example, e-mail, text, patient-oriented web portal, and/or provider-oriented web portal corresponding to each affected clinic.

The records integration module 320 may be configured to update or populate EHRs with processed diagnostic data and other information related to implantable medical devices by, for example, embedding web links into the EHR of a patient that facilitate access to the processed device-related data. Such data may include, for example, dates of the diagnostics performed on the implantable medical device, numerical data and/or graphs of the diagnostics results, recommended and/or performed actions based on the diagnostic results, the health or biological response of the patient to the operation of the device based on data detected by the device, and so on.

Turning now to FIG. 4-17, various examples of a portal or user interface is provided for accessing, analyzing, observing, or otherwise managing information and data received at the medical device platform 204 from one or more implantable medical devices. In one particular implementation, the user interface is displayed on a user device 108, such as that described above with relation to FIG. 1. The various user interfaces displayed on the user device 108 may be accessed through network 106 by the user device and executed by the server or servers 112 of the system 100. Further, one or more medical devices 104, such as one or more implantable medical devices from one or more patients, may provide information or other operational data to the medical device manager 102 and stored in database 110. For example, utilizing a Health Level 7 (HL7) protocol, the medical device manager 102 may receive communications from device manufacturer remote transmissions that contain device and/or patient specific data and device fields for device type and model. The medical device manager 102 may translate or otherwise normalize this data into data that is presented through a user interface. In another example, a patient may provide data or information to the medical device manager 102 through the interface directly or to a clinical staff for entry into the manager. This information may then be processed in various ways by the medical device manager 102 and presented or managed by the user through the user interface. Thus, a user (such as a nurse or doctor of a clinic) can receive, access, analyze, and/or manage data from the one or more medical devices 104 per patient or across multiple patients in a manner that has been previously unavailable.

As described herein, the medical device manager 102 manages CIED device transmissions and interrogations, including both in-office interrogations and remote interrogations. In one implementation, in-office interrogations utilize an in-office upload interface generated by the medical device manager 102, with which a user may drop or select one or more files for import. The files may be accessed over a network, via memory (e.g., a flash drive), and/or the like. Once the file(s) are selected, the interface may generate a visualization of a progress of the upload as the medical device manager 102 processes the interrogation data. In one implementation, an interstitial interface is generated, which may be used to verify, add, or edit encounter info, including, without limitation, an encounter date corresponding to the data extraction, a patient name, a patient date of birth, a clinic name, a device manufacturer, a device type, and a device serial number. If data is missing, the user can enter it via the interstitial interface. The medical device manager 102 may determine if the patient is a new or existing patient and proceed accordingly. Multiple visualizations are provided via the interface including a progress of processing the interrogation data, options for proceeding, editing, or canceling, and a progress of uploading the data to the medical device manager 102. The user may further be provided with options, including whether to upload the associated PDF from the interrogation. During the processing and upload, the data file is parsed and discrete data is imported from the parsed data file. Upon import, the user can add, edit, and review the imported data via a user interface. Where the PDF is imported, it may be presented along with the imported data or otherwise be accessible via the interface. The imported data may be automatically or manually saved.

Stated differently, in one implementation, each device manufacturer has manufacturer-specific programmers (pgms) located in a clinician office. A programmer is an in-office desktop device that interrogates ("pulls" or "reads") patient device data via a handheld magnetic device held in close proximity to a medical device 104. The programmer data is available for export to a secure memory, such as a Universal Serial Bus (USB) drive. This data often includes many files and extraneous info. The data is imported by the medical device manager 102 through a variety of mechanisms, such as a drag and drop or manual import file selection. The medical device manager 102 then parses the data for various markers. Once imported, the encounter (transmission) is processed to automatically identify device and patient specific data, and/or other device specific data fields.

More particularly, once files are ready for upload, the medical device manager 102 parses the data file for key identifiers. After user confirmation, the medical device manager 102 automatically populates fields with the data from the parsed data file, including packaged PDF reports each vendor provides from the programmer. In one implementation, as described herein, the medical device manager 102 generates a data file from an interrogation, performs an initial upload of the data file, identifies a patient and a device, parses the data file, uploads the parsed data file, generates and transmission overview from the parsed data file, and generates a workflow.

In one implementation, the data file is generated following an in-office encounter during a patient visit, at the time of implant, during a check, and/or the like. The data file may be generated by the medical device manager 102, by a manufacturer programmer, and/or the like. The encounter may consist of reading the device, testing performance of different parameters, changing settings on the device (re programming), and/or the like using a manufacturer programmer. In another implementation, the data file is generated from a remote transmission. The data file, including associated PDFs, may be saved to memory for use in uploading or otherwise transmitted to the medical device manager 102. The user may select whether to upload the PDF or not. In some implementations, the medical device manager 102 limits the upload to a single identified data file.

During the initial upload of the data file, the data files are identified and verified. Each manufacturer has its own set of data file types that the programmer generates, along with a PDF. Further, each manufacturer may have a plurality of data file subtypes. The file types may further have variations that may be determined by the device or programmer firmware version, resulting in a plethora of file types. The medical device manager 102 identifies the firmware version and initiates parsing the data file in a position based on the identified firmware version.

As relevant data is not easily accessible due to the files being difficult to read, the data being scattered, and often encoded, the medical device manager 102 parses the data in a plurality of parsing stages. Following the initial upload, the medical device manager 102 runs a series of checks against a plurality of identifiers. In one implementation, the identifiers include, without limitation, a serial number, a device model, a manufacturer, and a clinic. Based on the results, the medical device manager 102 performs an initial parsing of the data file by determining whether the data file corresponds to an existing patient, a new patient, an existing patient but a new device, or if the patient exists but is attached to another clinic. If the patient is existing, the data file is associated with a corresponding current patient record and if the data file is associated with a new patient, a new patient record is generated. During the initial parsing, the medical device manager 102 parses file types, file formats, and data content within the data file. In one implementation, the medical device manager 102 parses the data file to locate key identifiers, including, but not limited to, first name, last Name, data of birth, manufacturer, device, transmission date, and serial number. Based on the results of the initial parsing, the medical device manager 102 may notify the user if the patient is new, exists, or meets other conditions, permitting the user to take action, if desired using the interstitial interface. In one implementation, the user may verify the information from the initial parsing to determine whether to proceed with generating a record (e.g., docket) or cancel to return to a populated dropzone. After proceeding with generating the record, the medical device manager 102 performs a second parsing by analyzing and extracting discrete data based on extensive data mapping. Following the second parsing, the medical device manager 102 populates a patient panel with the parsed data. The data points included in the parsed data may range from 6-200.

In one implementation, the patient panel includes the parsed data visualized with the associated PDF in a transmission overview interface. A user may edit, remove, or add information to the prepopulated patient panel. Where the transmission is associated with a new patient, the patient panel may include, without limitation, device type, manufacturer, and serial number, and a new patient record is generated showing a single in-office transmission associated with the upload. Where the transmission is associated with an existing patient, a set of key identifiers are matched. The patient record shows that an in-office transmission is added to a stack of in-office interrogations, if one exists. If only a stack of remote transmissions exits or there is no current in-office interrogation stack, the medical device manager 102 generates a new docket instance. As such, the medical device manager 102 may generate and track workflows for in-office interrogations separate from remote interrogations. As such, the medical device manager 102 may generate an in-office docket and a remote docket, with the in-office docket including unique CPT and ICD-10 codes.

In one implementation, the medical device manager 102 generates a report (e.g., docket) documenting a trail of patient in-office interrogation review and impressions by a technician and approval of a provider. The report is generated by the medical device manager 102 for in-office or remote interrogation by combining patient information, proprietary historical presentation, a transmitted PDF file if attached by the reviewer, and/or the like. The report is generated in the cloud by the medical device manager 102 and may be stored or packaged and made available as a PDF download.

In one implementation, for remote interrogations, the medical device manager 102 uses HL7 communication protocol and IDCO data standard to receive data files from device manufacturer remote transmissions that contain device and patient specific data and device fields for device type and model. The medical device manager 102 builds secure connections to the manufacturers using published and defined communication pathways established by those manufacturers. The device transmissions sent from the patient devices 104 are first received by the manufacturers and then the data file, including the manufacturer PDF reports are received by the medical device manager 102. Upon receipt, the medical device manager 102 qualifies each new medical device 104 to verify the integrity of the data and transmission receipt through a plurality of processing stages. In one implementation, for either in-office interrogations or remote interrogations, the medical device manager 102 performs HL7 data extraction through data mapping and IDCO data normalization and generates device setting calculations and normalization.

In one implementation, the medical device manager 102 extracts unidentified HL7 data by mapping unique data fields during the data mapping. In every case, the medical device manager 102 identifies and verifies the data. For example, some manufacturers send parameters to a notes section of a transmission data file, while others store this information elsewhere. The medical device manager 102 parses the data file to identify the relevant data, extract the relevant data, combine it with other data, and present it in a manufacturer independent format in the patient panel. The medical device manager 102 may parse the data file in a manner that manufacturer specific terms are presented intact, along with any relevant backup math or information.

During the IDCO data normalization, the medical device manager 102 identifies and normalizes event types. More particularly, every manufacturer identifies a same event type with a different descriptor. As such, the medical device manager 102 reviews and normalizes every manufacturer method of transmitting the same data with varying descriptors. For example, the event NSVT may be represented as NonSusVT, Non SVT, NSVT, NonSust VT, and/or the like, based on the manufacturer. Further, HL7 is cryptic, and the medical device manager 102 aggregates shock amounts and maps terms in HL7 to terms used in the PDF from each manufacturer. Moreover, names of zones vary between manufacturers and are use differently in PDFs. As such, the medical device manager 102 takes the HL7 type names and maps these to the terms used in the PDFs across all manufacturers. In the patient report, the data is normalized in display across manufacturers. In one implementation, over 200 unique data fields for each manufacturer are normalized by the medical device manager 102 to present a common and accurate display to clinical user across disparate manufacturers and devices.

In one implementation, the manufacturers send device data in bulk via HL7 in the IDCO format. The manufacturer sends all data fields, even though the device may be programmed to be managed by only one of those fields. The PDF reports sent via IDCO correctly display the relevant "programmed" data fields. As such, the medical device manager 102 inspects each transmission and correlates the program setting to the corresponding data fields to accurately display the data that corresponds to the program setting during device setting calculations. The IDCO standard does not include association of program setting to data sensing fields. Not all data is readily available and needs to be massaged by the medical device manager 102. For example, the medical device manager 102 may analyze impedance to see how the device is programmed. The medical device manager 102 examines the HL7 data to determine the proper measurement type, including ring, tip, coil, can, etc. Measurements between these components are given. If the device is programmed Ring→Tip, the medical device manager 102 determines that impedance is the proper calculation for that medical device 104.

Further, the medical device manager 102 may group shock amounts and list them according to PDF display. The medical device manager 102 assembles the data to match the PDF. Treatment types (e.g., burst, shock) and charge amounts in Joules are compiled. The medical device manager 102 also maps HL7 values to more meaningful values the manufacturer uses in PDF, as HL7 does not always have the values used in the PDF. For example, some Rx Off is displayed in the PDF, which is not a passed value. In order to display the value, the medical device manager 102 analyzes other factors and data. The medical device manager 102 normalizes the HL7 values. For example, manufacturers have different descriptors for VT1 and VT2. The medical device manager 102 shortens them, remaps them or looks at other data, to identify the values as VT1 or VT2. IDCO data set is loose and poorly defined and must be normalized by the medical device manager 102 to reflect device settings. In one example, the medical device manager 102 obtains discrete data and pieces it together. In some cases, the medical device manager 102 identifies values in other fields to reach the conclusion identified in the PDF. In one implementation, the medical device manager 102 parses the fields and generates a phrase, which is used to know what fields to group together, know if a zone is off, monitor or active. S-ICD's have unique zones that the medical device manager 102 populates unilaterally from knowledge of the device, as this information is not included in the data file.

Some manufacturers store all device readings for the medical devices 104 in perpetuity over the life of the patient and/or device, which may result in reporting of prior events when sending new event data. During device setting normalization, the medical device manager 102 filters this data so that the new events that have not been previously received are highlighted. Some manufacturers, reset these counters after every transmission, so the medical device manager 102 filters selectively based on the data management structure of each medical device 104. If the event has been reported before, the medical device manager 102 buckets or otherwise labels the event as a legacy event, meaning that the event has occurred outside of the time frame that the transmission covers (e.g., between the send date and the send date of the previous transmission). Since the information is in the HL7/IDCO data set, the medical device manager 102 may still report the event, but the medical device manager 102 does not factor it into the transmission as a current event because it would have already been clinically acted upon. Other items come in as episodes but are not (e.g., periodic EGMs), and the medical device manager 102 scrubs over 20 episode types between manufacturers that are not episodes at all.

Following the receipt, parsing, and uploading of the data file, the medical device manager 102 generates a transmission overview and a report (e.g., docket) that initiates a workflow managed by the medical device manager 102 through a series of interfaces as described herein, for example with reference to FIGS. 4-17.

Figure 4:
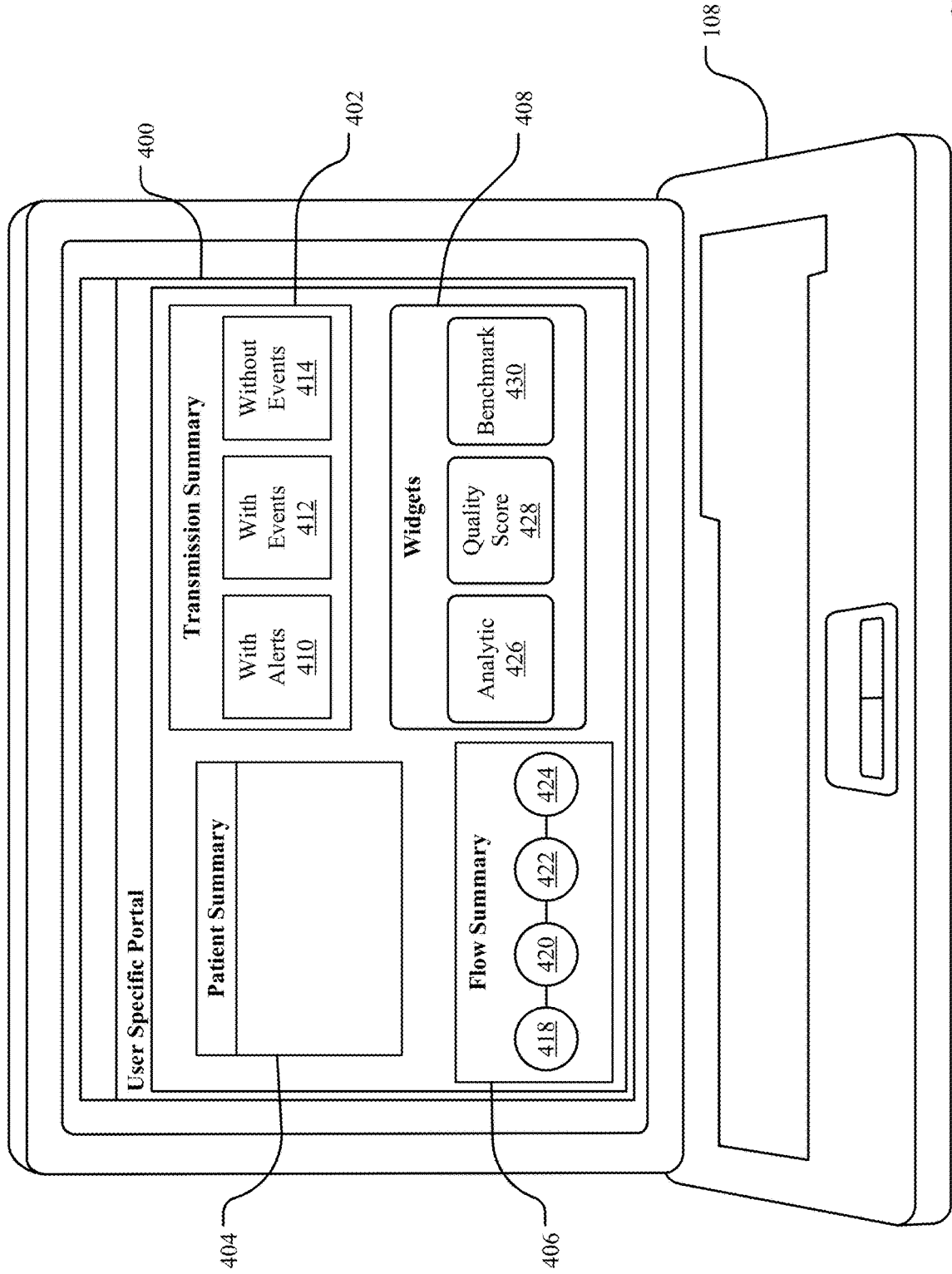
FIG. 4 shows an example device management user specific interface for managing patient medical devices.

FIG. 4 shows an example device management user specific interface for managing patient medical device data. In general, the user interface 400 of FIG. 4 provides data and data management options that are user-specific portal to the user's role (such as a nurse or doctor of a clinic or a patient analyzing their own device data). Thus, the data management options displayed in the user interface 400 (one example of which is illustrated in FIG. 4) may be altered or different depending upon the role of the user accessing the user interface. The medical device manager 102 may determine the style and/or content of the user interface 400 based on log-in information provided to the system by the user upon accessing the system. Other interfaces discussed in more detail below may or may not be available to particular users based on similar identifying information.

In the particular example illustrated in FIG. 4, several presentations of medical device information and data management options are provided. In particular, the user interface 400 may include a transmission summary portion that provides an indication of the number of transmissions from medical devices received over a period of time. For example, the transmission summary 402 may include a count for a total number of transmissions received since last log-in by the user, for the current 24 hour period, for the lifetime of the medical device manager 102, and the like. Further, the transmission summary or tracker 402 may sub-divide the transmission count into one or more categories. In the example illustrated, the transmission summary portion 402 may include the number of transmissions received with alerts 410, with events 412, and/or without events 414. As mentioned above, the transmissions may be received from one or more medical devices in communication with the medical device manager 102. In one example, a patient with an implantable device may visit a clinic to provide the data to the medical device manager 102 from the device. In another example, the medical device may wirelessly or remotely provide the data to the medical device manager 102. Regardless of how the data is received, the transmission summary 402 of the user interface 400 provides summary or analysis of the data received from the medical devices over a period of time.

The user interface 400 may also include a patient summary portion 404. Again, the information displayed or provided through this portion 404 may be based on the user role. In one example, the patient summary section 404 may provide a listing of all patients whose devices have transmitted performance data to the medical device manager 102 over the period of time if the user is a clinic employee or otherwise has permission to access multiple patient information. Such a listing may include a number of transmissions received per patient and may or may not include a color indication associated with the type of transmission received. In another example, the patient summary section 404 may provide only a particular patient's information if the user is that patient. In one implementation, the patient summary information 404 may be displayed by patient information instead of by transmission information and may display a number of device transmissions received. Alternatively, the information may be displayed by transmission types or number of transmissions such that a collection of transmission per patient may not be displayed. As explained below, each listing of patient information in the patient summary 404 may be tied or associated with a workflow for that patient to be completed by a clinic employee.

Another portion of the user interface 400 may provide a flow summary 406 that summarizes a completion status for one or more of the events displayed in the patient summary 404 (or from any other collection of workflows to be completed). As should be appreciated, transmissions received from a medical device may initiate a workflow to analyze or address the transmission, such as those transmissions with an alert or an event. The flow summary section 406 may provide a summary of the status of workflows, from open workflows 418, pending action workflows 420, for approval workflows 422, and/or completed workflows 424. The flow summary 406 may include any number of workflow stages 418-424 and a number of workflows at each stage may be illustrated in the summary. For clinic staff, the flow summary 406 may provide an overview of potential workflow activity for any period of time for better workflow management.

Further, the user interface 400 may include a widget portion 408 that provides analytics of received transmissions to give insight of received data organized around clinics, patients, devices, quality scores, burden scores, target tracking, etc. In general, the widgets 408 may include analytic information 426, quality score information 428, and benchmark information 430, although fewer or more widgets may be available through the widget portion. The operation and aim the various widgets 408 of the user interface 400 are discussed in more detail below with reference to FIGS. 5-7.

Figure 5:
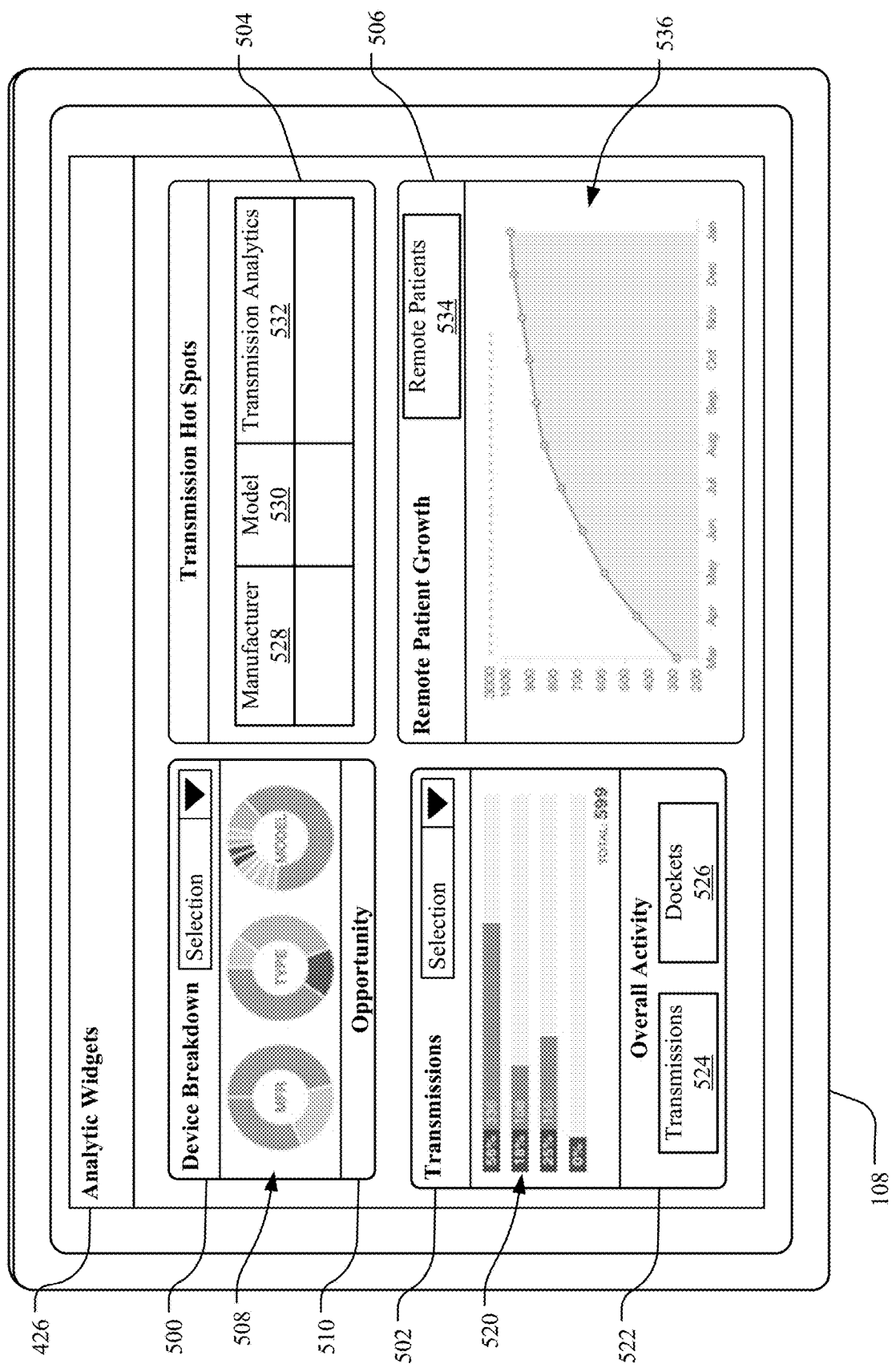
FIG. 5 shows an example analytic widgets user interface for managing patient medical devices.

FIG. 5 is an illustration showing an example analytic widget user interface 426 for managing patient medical devices. In general, the analytics interface 426 may provide one or more automated snapshots of trends for transmissions associated with a particular clinic. For example, a device breakdown section 500 may provide a drop-down menu (or other selection mechanism) to select to view transmission information breakdown sorted by patients or by transmissions. Once a category is selected, one or more device breakdown graphs 508 may be presented that provide an indication of device-specific information for the received transmissions, including but not limited to, breakdown by device manufacturer, breakdown by device type, and/or breakdown by device model. Additional or fewer breakdown graphs 508 may be included in the user interface, also sortable based on patient or transmission.

The user interface 426 may also include an opportunity score 510 presented to a user of the interface. In one implementation, the opportunity score 510 provides a device count applied to a normalizing standard of care to illustrate a max reimbursement opportunity in dollars or clinical relative value units (RVUs). For example, the medical device manager 102 may determine a maximum billing allowed for each medical device that includes an annual in-office follow-up frequency and remote follow-up frequency. These may be multiplied by a reimbursement rate and multiplied again by the amount of patients for that particular device. This calculation may be presented in the user interface 426 through the opportunity 510 portion.

In some implementation, the analytic widget interface 426 may include a transmissions summary portion 502. The transmission summary portion 502 may include a drop-down menu (or other selection mechanism) to select a particular period or length of time to apply to the received transmissions. For example, the menu may provide for the selection of the previous 30 days of transmissions, 15 days of transmission, 24 hours of transmissions, etc. Once the timeframe is selected, the transmissions portion 502 may illustrate or provide an indication of percentage of total volume of transmissions received over the selected timeframe, perhaps sorted by manufacturer or vendor. Other mechanisms for illustrating the number of transmission received over the selected timeframe may also be displayed.

The transmissions summary portion 502 may also include a summary of overall activity of the user logged into the interface 426. For example, an indication of the total number of transmissions 524 for the selected timeframe may be displayed, as well as a number of dockets 526 included in the displayed transmissions. A total number of transmissions received in the selected timeframe may also be displayed, in some implementations.

Similarly, the analytic widgets interface 426 may also include transmission hot spots portion 504. In this portion 504, a listing of transmission burdens may be displayed based on the number of transmissions received per device type. The displayed information may be sortable by manufacturer 528, model type 530, or transmission analytics 532, in one implementation. In general, the transmission hot spots portion 504 may identify high demanding devices and patient populations to reflect patient/device densities within the received medical device transmissions.

Also included in the analytics widgets interface 426 may be a remote patient growth portion 506. In general, the remote patient growth portion 506 provides data and graphs on the total number of patients from which device transmissions is received and month-to-month changes in patient numbers. Thus, the portion 506 may include an indication of the total number of remote patients 534 included in the data displayed in the interface, as well as a graph 536 of illustrating the change of patient numbers over a period of time. In one implementation, the graph 536 may illustrate a month-by-month trend in patient numbers included in the user interface.

Figure 6:
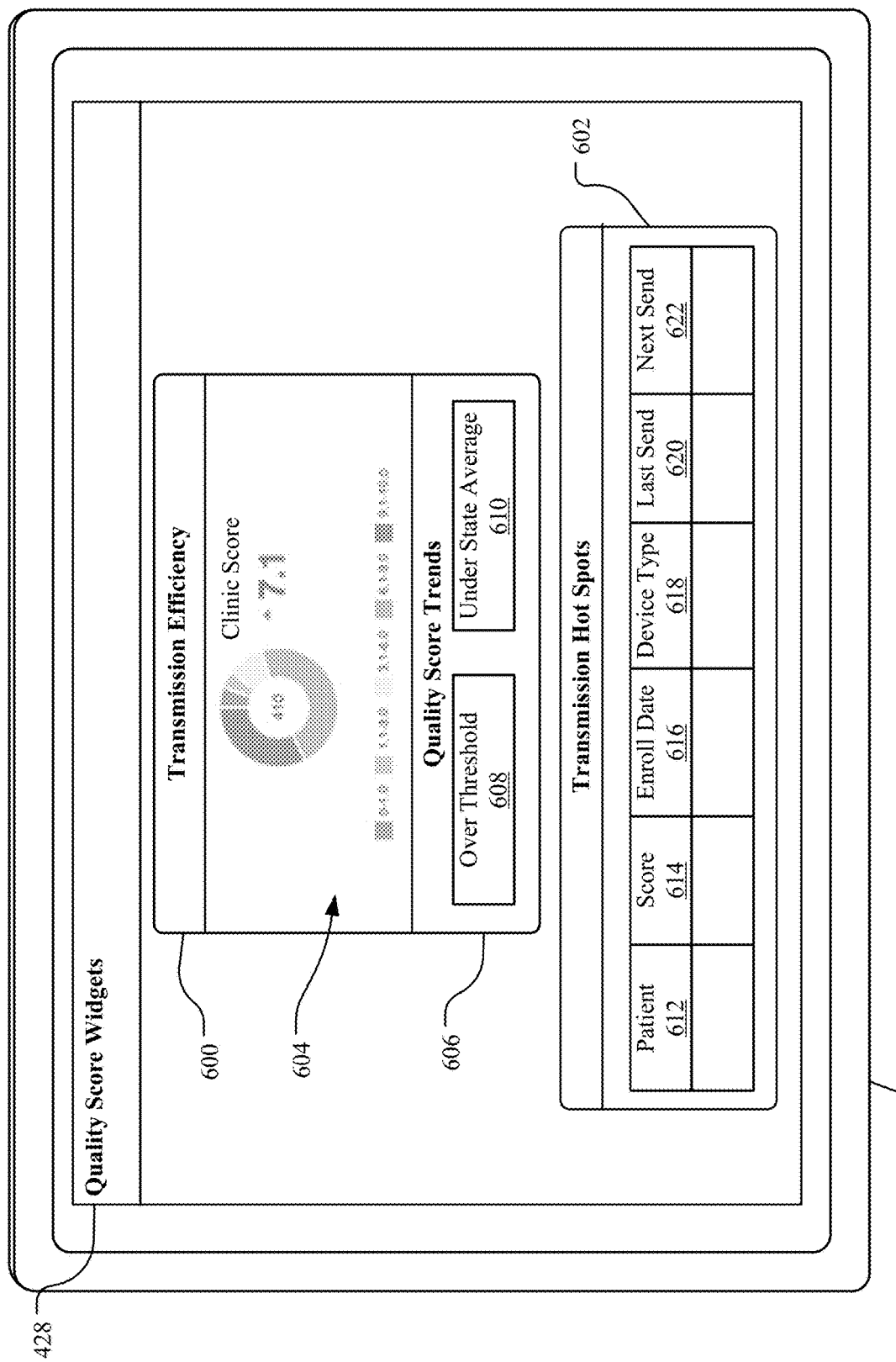
FIG. 6 shows an example quality score widgets user interface for managing patient medical devices.

As discussed above, the user interface 400 illustrated in FIG. 4 may further include a link or other indicator of a quality score 428. FIG. 6 shows an example quality score widgets user interface 428 for managing patient medical devices. This interface may be displayed on the user device 108 upon selection of the quality score widget from user interface 400. In general, the quality score widget interface 428 provides an indication or calculation of a clinic's performance as measured against an industry recommendation. For example, a particular industry standard may suggest that a particular device be checked remotely every four times annually (e.g., once every 91 days) with two in-office checks (e.g., once every 180 days). The medical device manager 102 may be automatically or manually calibrated according to new standards of care or changes to existing standards of care. The medical device manager 102 may therefore apply weights to particular events (e.g., missing a transmission, not scheduling enough transmissions compared to industry standard, transmitting too frequently, frequent non-billable dockets, transmissions that sit idle for too long, speed of transmission management, etc.) and calculate a quality score for that device/patient. The speed of transmission management may involve docket creation, approvals, and billing window achievements (e.g., processing a check within the standard of care window). Individual scores for devices or patients may, after calculation, be displayed in the quality score widget interface 428. For example, the interface 428 may include a score table 602 listing a patient's name 612, a calculated quality score 614 against a determined industry standard, a patient enrollment date 616, an indicator of the device type 618, the date and time of the last transmission 620, and a data and time for the next scheduled transmission 622. In one example, the quality score 614 for each patient may be normalized between 0-10.

The quality score widget interface 428 may also provide summaries or other calculations for the quality scores of each patient included in the patient score table 602 in a transmission efficiency portion 600. For example, the transmission efficiency portion 600 may include an overall quality score 604 for the clinic associated with the user of the interface. The clinic score 604 may provide an indication or graph of the number of patient quality scores that fall within predetermined ranges, such as the number of quality scores in the list 602 between 9.1-10.0, 6.1-9.0, 3.1-6.0, etc. Further, the clinic quality score 604 may include an overall average clinic score for the patients of the clinic. Further still, the transmission efficiency portion 600 may include an indication of a number or percentage of quality scores in the list 602 that exceed a defined threshold score in portion 608 and/or the number or percentage of quality scores below an average quality score for the state of the clinic in portion 610. The information provided in the quality score widget interface 428 may provide a clinic staff an indication of the overall performance of the clinic in comparison to an industry standard to indicate when improvement in patient service is needed.

Figure 7:
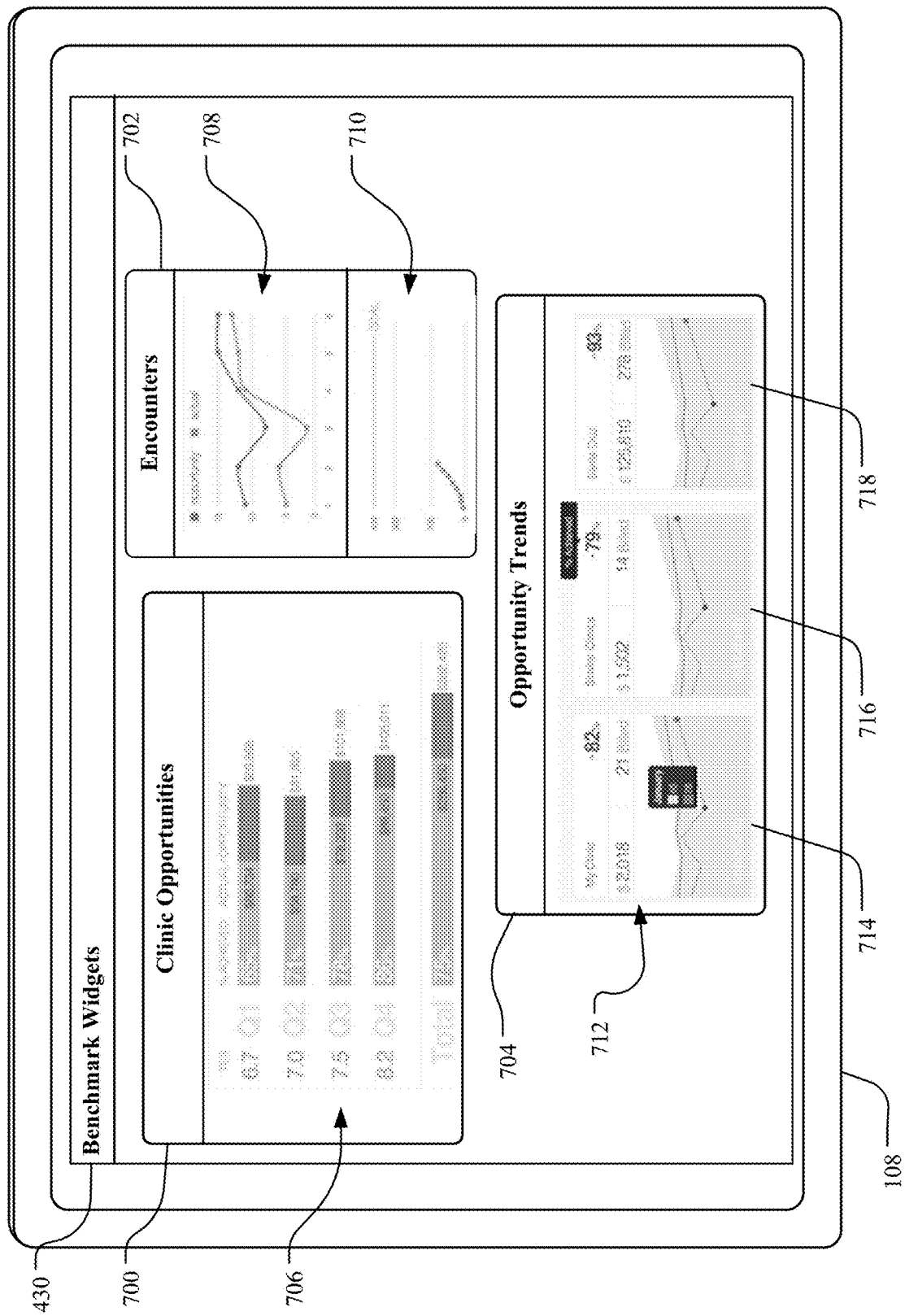
FIG. 7 shows an example quality benchmark widgets user interface for managing patient medical devices.

As also discussed above, the user interface 400 illustrated in FIG. 4 may further include a link or other indicator of a benchmark widget interface 420. FIG. 7 shows an example benchmark widget user interface 420 for managing patient medical devices. This interface 430 may be displayed on the user device 108 upon selection of the quality score widget from user interface 400. In general, the benchmark widget interface 430 provides analytics that reflect quality, goal setting, benchmarks, and performance towards goals specific to a particular clinic. In the implementation illustrated in FIG. 7, the benchmark widget interface 430 includes a clinic opportunities portion 700 that includes one or more clinic billable metrics 706 over a period of time. For example, the medical device manager 102 may calculate or otherwise determine which received transmissions are billable and provide metrics on such billable transmissions to aid the clinic in prioritizing operations. In one specific implementation, the clinic opportunities portion 700 includes a number of transmissions billed, a number of opportunities for billing a transmission, and a percentage of actual billed of opportunities. This may be presented per quarter and for the total number of transmissions received.

In one implementation, the medical device manager 102 calculates billing opportunities based on applicable standards of care adopted by insurance payors in the form of a reimbursement schedule for services rendered. A billing opportunity may be calculated by multiplying a reimbursement rate by a frequency of available reimbursements (e.g., a number of treatments allowed to be billed per billing cycle) and by a number of patients. For example, for an ICD device where the standard of care is four remote interrogations at a rate is $94 and two in-office interrogations at a rate of $88, an annual opportunity is 4×$94+2×$88=$552 per ICD patient. Configuration tools may be used to allow a user to set target ranges for care frequency and rates of reimbursement, which may be the same or different than the standard of care, as clinics may elect to care for a patient more or less than the standard of care due to a variety of unique circumstances and have different reimbursement rates. Finally, the medical device manager 102 may identify a billing window by counting the days since last transmission bill date reflecting reimbursement guidelines for minimum and maximum days (e.g., 30 or 90) between billable events. The billing window may be device type dependent. For example, ICD remote care reimbursement is currently allowed every 90 days. The medical device manager 102 calculates if a transmission is billable is based off of that 90 day interval between billings. Standard of care publications may set the date frequency and allowable intervals by device and treatment types, and the medical device manager 102 may update the billing window and billable opportunities based on any changes to the standard of care.

Another portion of benchmark widget interface 430 is an encounter portion 702 that provides a graph 708 of determined opportunities versus actual billing and a graph 710 that tracks progress toward a preset goal. Another portion provides trends for billing opportunities 704 that show a collection of graphs 712 providing tracking of opportunities for the clinic versus other clinics in the community or multiple clinic sites. Thus, a first graph 714 may provide clinic opportunities of the clinic of the user, a second graph 716 may provide opportunities for a similar clinic, and a graph 718 for opportunities for a particular clinic in the community. This information may be utilized by the user to prioritize operations of the clinic based on the opportunity information displayed.

The benchmark widget interface 430 and/or another interface may further provide community analytics. As a cloud-based product, the medical device manager 102 can leverage a community of users, patient outcomes, and care dynamics to inform, educate, compare and share community analytics amongst users and community members. The community analytics may include, without limitation, a comparison of a clinic to a clinic with a high quality score; an identification of top performing clinics in various categories; an identification of any treatments that are effective for a particular patient type, device demographic, etc. across a community and applied to specific populations or specific clinics; and/or the like. In one implementation, the community analytics may include a clinic graph showing billing opportunities over a time period with a dollar amount reimbursed, a number billed, and a percentage billed. A similar clinics graph may be presented summarizing other similarly situated clinics, and other clinic graphs particular to other clinics may also be included for comparison. In one implementation, a regression analysis algorithm identifies unknown trends, associations, and opportunities for patient care. Comparative analysis involves database calculations to identify performance benchmarks, outputs, and to generate comparisons for individual patients, clinics, or regions. Target and/or actual opportunities or analytics can be applied and visually represented against community trend lines, actuals, and top performers.

Also included in the user interface 400 of FIG. 4 as discussed above is the patient summary portion 404. As described, the patient summary section 404 may provide a listing of patients whose devices have transmitted performance data to the medical device manager 102 over the period of time if the user is a clinic employee or otherwise has permission to access multiple patient information. The number of patient listings in the patient summary interface 800 may be selectable through a drop-down selector 802, or any other type of selectable mechanism. Through the menu 802, the user may select to view any subset or all of a total number of patient summaries. The total number of available patient summaries may also be indicated 804 in the user interface 800. The patient summary portion 404 provides an aggregated view of all transmission ready for processing, which may be segregated by a visual identifier (e.g., color coding) indicating a level of transmission severity. Each is selectable to direct the user to a patient list with a filter activated according to the level of transmission severity.

Figure 8:
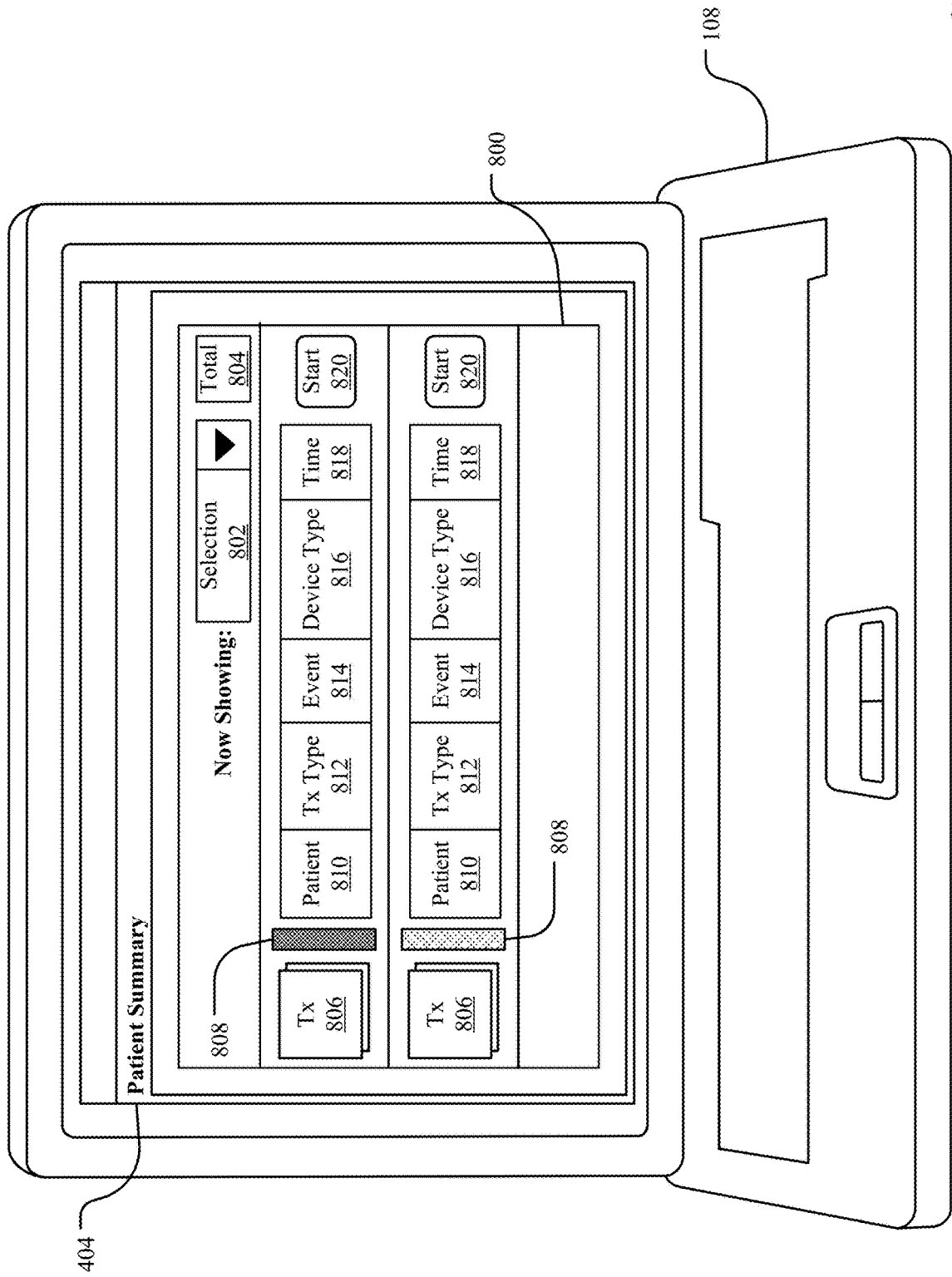
FIG. 8 shows an example patient summary user interface for managing patient medical devices.

In one implementation, the patient summary interface 800 may include a listing of patients of a clinic and respective transmission data for each patient. As illustrated in FIG. 8, each patient listing may include a total number of transmissions 806 associated with the particular patient that have been received at the medical device manager 102, a patient name 810, a particular transmission type 812, an event 814 associated with the transmission or with the last received transmission, a device type 816, and a time 818 that the particular transmission or a last received transmission from the patient was received. Further, each patient listing in the patient summary interface 400 may include a color indicator 808 that identifies a severity of transmission functionality. For example, a red color indicator may indicate a transmission with an alert, a yellow indicator may indicate a transmission with an event sent from the manufacturer (HL7), a green indicator may indicate a transmission with no event during the time span the transmission covers, and a gray color may indicate that the transmission has been processed (such as in response to approval by a clinic doctor or team leader). In a stack of transmissions, severity determines the overall color of the stack with green being less than yellow which is less than red. As such, the stack will be assigned the color indicator 808 based on the highest level of severity, regardless of the number of transmissions assigned each color in the stack.

Past transmissions, including a transmission count for a manufacturer over the specified time period, may be displayed including an overall activity, device breakdown by type, and device breakdown by model. The overall activity may include transmission and docket count for a particular user, including how many transmissions the user has processed and how many dockets the user has created. The device breakdown type may be by HL7 device type breaking down, for example, into ILF, ICD, PM, CRT-P, CRT-D, and other. Numbers for patients and transmissions may be included, with the data included in IDCO format and prompted for manual entry. Gaps in the data may be highlighted. The device breakdown by model may be by HL7 model type with the remaining grouped into other. The data may be included in the IDCO format and prompted for manual entry. Gaps in the data may be highlighted.

Each patient or transmission listing in the patient summary interface 800 may be processed by a clinic staff or any other user of the medical device manager 102. Processing of the transmission may include generating a docket or workflow for each transmission that may include various activities by the medical device manager 102 and/or clinic staff. For example, some workflows for a transmission may accept signatures or other acknowledgments from clinic staff to indicate that the transmission has been analyzed and approved. Other activities may include, but are not limited to, scheduling follow-up exams based on the received transmission, billing of the patient, discussing treatment options with the patient, transmitting one or more alerts to clinic staff, ordering replacement components for a particular device, reporting operational status and information to manufacturers, generating one or more documents for storage, and the like. The workflows generated for each transmission may include any number of activities or processes to be performed before a transmission in considered to be processed. To begin such workflows or processing, each patient transmission listing in the patient summary interface 800 may include a workflow or processing start button 820 associated with each listing. Selection of the start button 820 through an input device to the user's computing device 108 may begin the workflow process as described in more detail below. As such, through the patient summary interface 800 a clinic staff may process received device transmissions.

Figure 9:
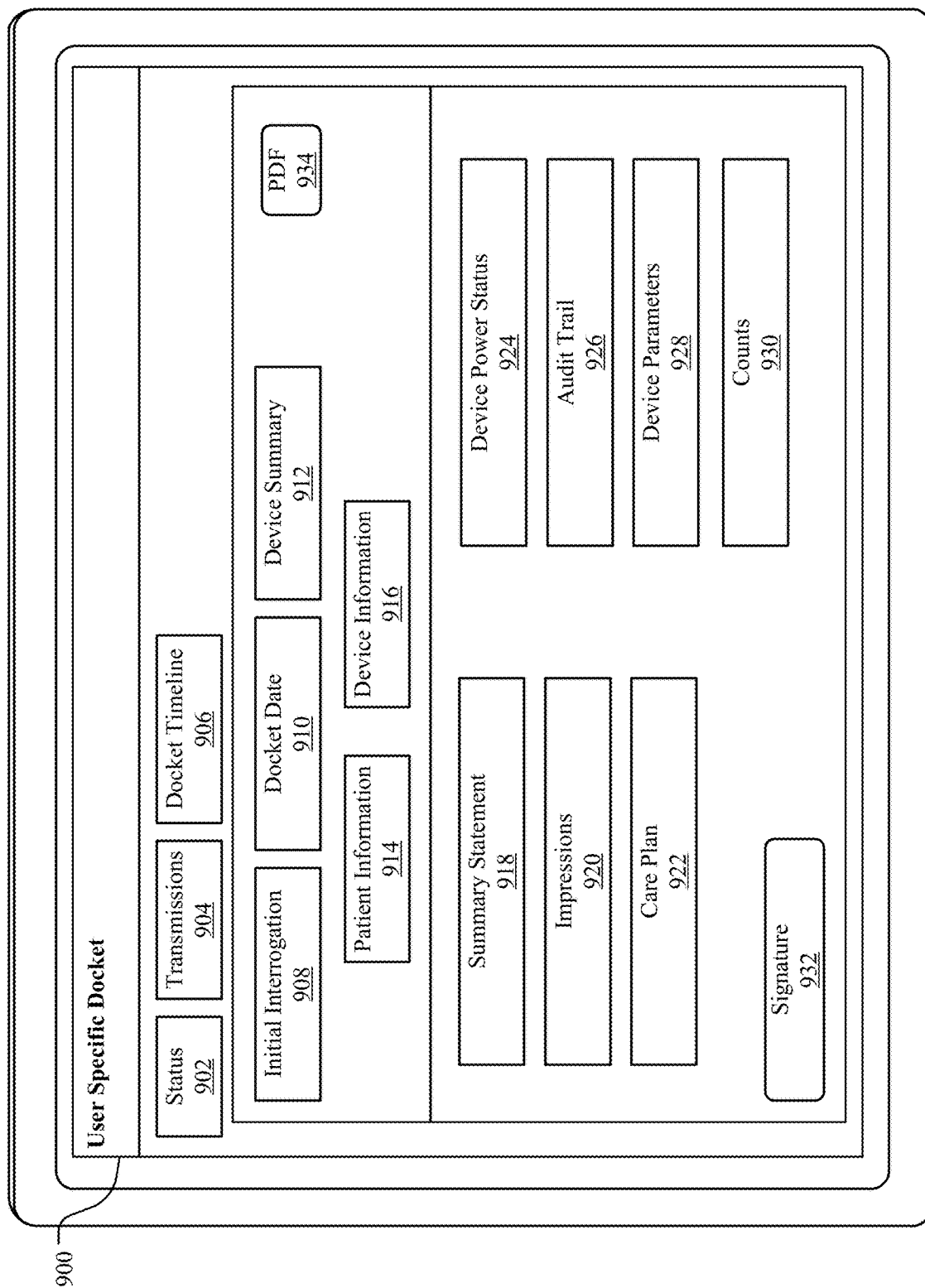
FIG. 9 shows an example user specific docket user interface for managing patient medical devices.

FIG. 9 shows an example user specific docket interface 900 for managing patient medical devices. In one implementation, the user specific docket interface 900 may be displayed on a user computing device 108 in response to selecting the start button 820 described above in the patient summary interface 800. Thus, the user specific docket interface 900 provides information pertaining to the corresponding device transmission received at the medical device manager 102. In general, the docket interface 900 provides an abridged interpretation, plan of action, and record of one or more patient device transmissions. Such dockets may be initiated, drafted, shared, and/or stored by the medical device manager 102. Although illustrated in FIG. 9, it should be appreciated that the user specific docket 900 may include fewer or more features, components, or portions as desired by an administrator of the medical device manager 102.

The example interface 900 illustrated in FIG. 9 includes portions for providing docket specific information for the processing of the docket. For example, the interface 900 may include an indication of the status 902 of the docket (cleared, in process, awaiting signature, just begun, etc.), a number of transmissions 904 associated with a particular patient device and/or the particular docket, and a docket timeline 906, which is discussed in more detail below. In addition, the interface 900 may include an indication of a user responsible for conducting an initial interrogation 908 in response to the transmission, a docket date 910, and a summary 912 of the number of transmissions from the device of the docket. Patient information 914 (such as a patient name or other identifier) and information of the device 916 from which the transmission was received may also be included.

The main body of the user specific docket interface 900 may include a portion for a summary statement 918 that summarizes the purpose of the docket (including number of transmissions being processed through the docket and/or the date the docket was generated), one or more conclusions or impressions 920 to provide guidance on responding to the received transmission, and a conclusion care plan 922 for treating the patient in response to one or more of the patient device transmissions received. A signature block 932 may also be included to collect signatures of clinic staff or other users of the interface 900 to approve the care plan 922 and/or conclusion impressions 920 for the received transmission.

In addition, device information and history may be provided through one or more portions of the interface 900. In the example shown, a device power status indicator 924 may provide an indication or estimate of a percentage of battery life of the medical device, an estimated lifespan of the battery, and a charge time. An audit trail 926 portion may provide a history of stored impressions for reference by the user of the interface 900. Further, a device parameters section 928 may provide specific device information and a counts 930 portion may provide counts of events or milestones in the operation of the device. All of this information may provide context a user of the user interface 900 in processing the docket in response to a received device transmission.

In some implementations of the user specific docket interface 900, a PDF selector 934 may be provided that allows the user to select to view or otherwise access the docket in a .pdf format. In general, the docket displayed in the user device 108 is in a Hypertext Markup Language (HTML) format. However, some users may prefer to view the docket in Portable Document Format (PDF). Through the selection of the PDF selector 934 of the interface 900, the medical device manager 102 may convert the docket into a PDF document accessible by the user.

Figure 10:
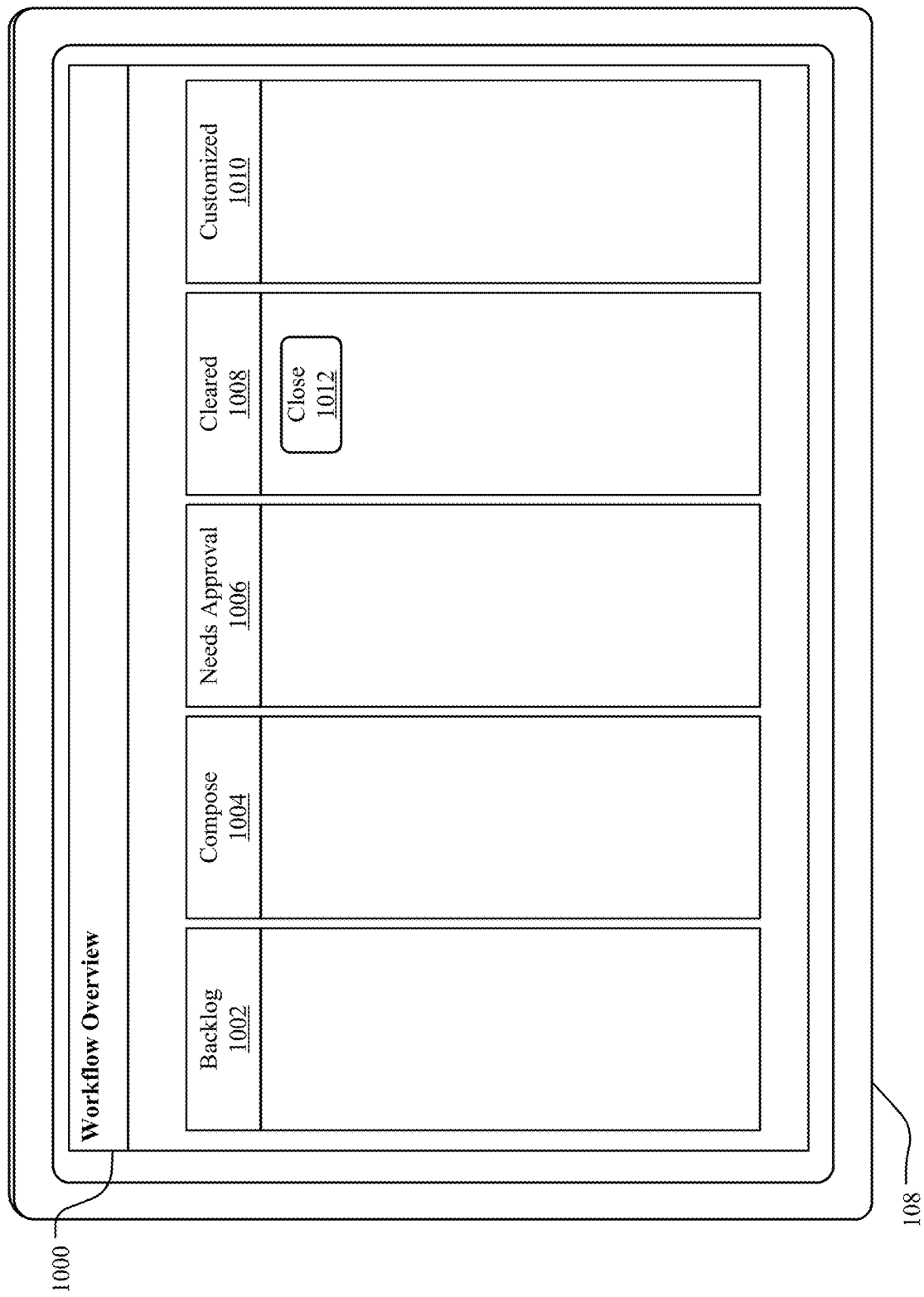
FIG. 10 shows an example workflow overview user interface for managing patient medical devices.

The medical device manager 102 provides for the handling of device transmissions through the entire transmission lifecycle, receipt to creation to submission to approval. FIG. 10 shows an example workflow overview user interface 1000 for managing patient medical devices. The interface 1000 includes lanes of processing that move transmission review and reporting from lane to lane as the processing of the transmission occurs. For example, any transmission that is received at the medical device manager 102 may be included in the workflow overview interface 1000. A backlog lane 1002 includes a listing of those transmissions that are received but not processed. Selecting to process the transmission at a later time moves the transmission to a compose 1004 processing lane for follow-up composition and finalization. When a docket is created for a transmission, a listing of the transmission is moved into the needs approval lane 1006 until one or more required signatures are applied to the docket and stored. Cleared or finalized transmission dockets may be listed in cleared lane 1008. Further, each cleared docket may be closed through a selection within the docket 1012 to remove the cleared dockets from the cleared processing lane 1008. One or more customized processing lanes 1010 may also be included and customized based on an administrator of the medical device manager 102. For example, a review lane may be added between the lames 1004 and 1006 to audit the workflow at that stage. Similarly, lanes may be removed. For example, the lane 1006 may be removed where saving a docket automatically approves it. As such, through the workflow overview interface 1000, a user may track the progress of the processing of one or more transmissions through the medical device manager 102 for better clinic management and workflow.

Figure 11:
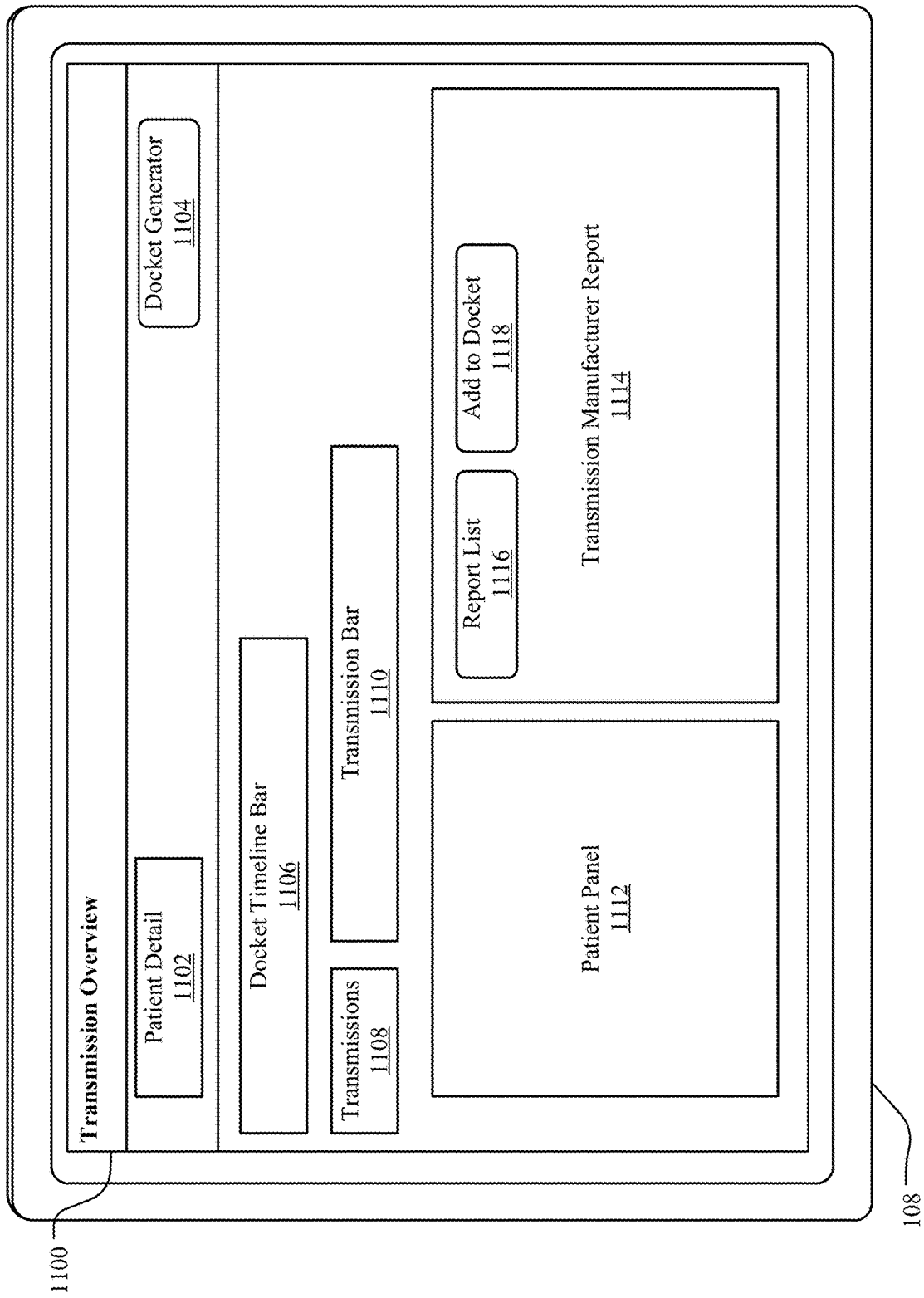
FIG. 11 shows an example transmission overview user interface for managing patient medical devices.

Processing of a transmission may begin at the interface 1100 illustrated in FIG. 11. In particular, the user may select a particular workflow interface 1000 of FIG. 10 to begin processing the transmission. The medical device manager 102 may then provide the transmission overview interface 1100 on the user's computing device 108 so that the user may begin to process the transmission. In the implementation shown, the transmission overview 1100 may include patient detail 1102 (such as the patient's name and/or some additional identifier), a docket generator 1104 selector for generating a docket for a patient transmission (discussed in more detail below with relation to FIG. 14), a docket timeline bar 1106, a total number of transmission 1108 for the patient, and a transmission bar 1110 for tracking the processing of dockets for the patient (discussed in more detail below with relation to FIG. 13), a patient panel providing information of the patient (discussed in more detail below with relation to FIG. 12), and a transmission manufacturer report portion 1114 providing information received from one or more manufacturers of medical devices. More or fewer components or portions may also be provided in the transmission overview interface 1100.

To begin processing a particular transmission, the user may select a transmission from the transmission bar 1110. In particular and turning to FIG. 13, the transmission overview interface 1100 may include a docket timeline bar 1106 that provides a user with access to every or some historical docket or report for a specific patient, as well as the transmissions that make up that docket. When a patient is identified in the patient detail 1102 of the transmission overview interface 1100, the historical dockets for that patient are made available to the user through the interface. In one implementation, the most recent dockets for the patient are displayed in the timeline 1106 such that the user may efficiently and quickly manage all transmissions for the patient in a single view. The docket timeline bar 1106 may include a series of boxes 1300 each with a date of a corresponding docket for that patient and may indicate a state of the docket, such as pending approval, open, or approved. Selection of a docket date from the docket timeline bar 1106 provides more information for the patient docket associated with that date in the transmission bar portion 1110 of the interface 1100.

Figure 13:
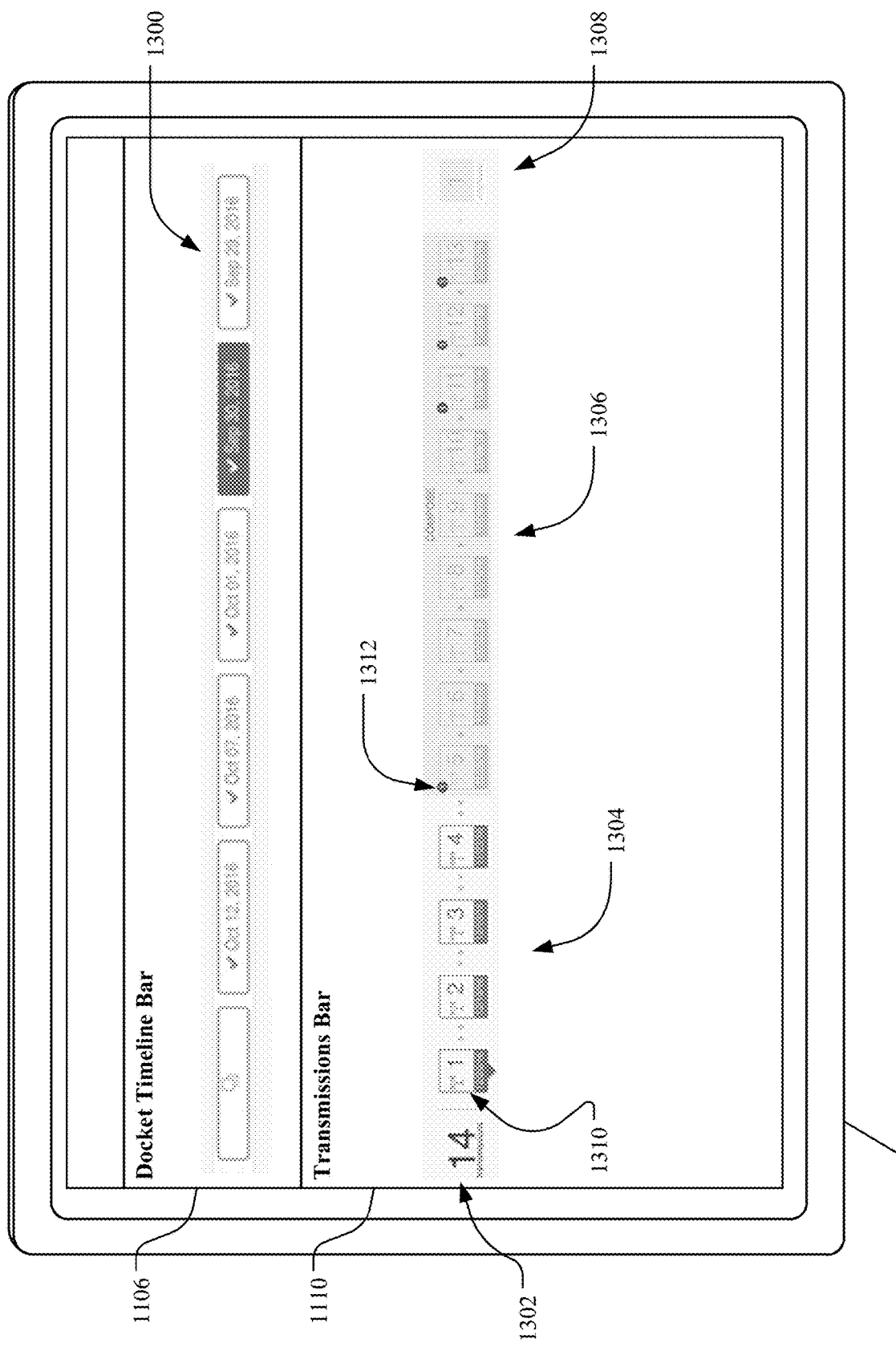
FIG. 13 shows an example docket timeline and transmissions bar user interface for managing patient medical devices.

As shown in FIG. 13, the transmission bar portion 1110 reflects one or more transmissions received for the selected patient. For the docket shown in FIG. 13, fourteen transmissions are included for the patient. Further, each transmission is illustrated in a transmission box 1310. Each transmission box 1310 may include several types of transmission information, including but not limited to, a transmission number, a transmission type (perhaps indicated through a specific icon), and a date received. Other indicators may also be present in the transmission boxes 1310, such as a transmission state (unviewed, viewed, compose, archived, active, etc.). Transmission boxes 1310 is one example of a transmission box colored to represent an active transmission, with boxes 1304 being colored to indicate another state, such as viewed. Further still, one or more transmission boxes 1306 may be shaded in a gray color (or other indicator) that indicates the related transmissions have a compose state (reflecting that some action has been taken to document the transmissions). Such boxes 1306 may also include an impression counter 1312 (represented in FIG. 13 as a circle bubble in the corner of the respective transmission box with a number). The impression counter 1312 indicates a number of impressions made to a patient docket and associated with the particular transmission of the transmission box in the transmission bar 1110. Finally, the transmission bar 1110 may also include any number of archived transmissions 1308 that reflect a transmission that a clinician has deemed irrelevant to the docket but is nonetheless retained with the docket for full transmission tracking and burden reporting.

Figure 12:
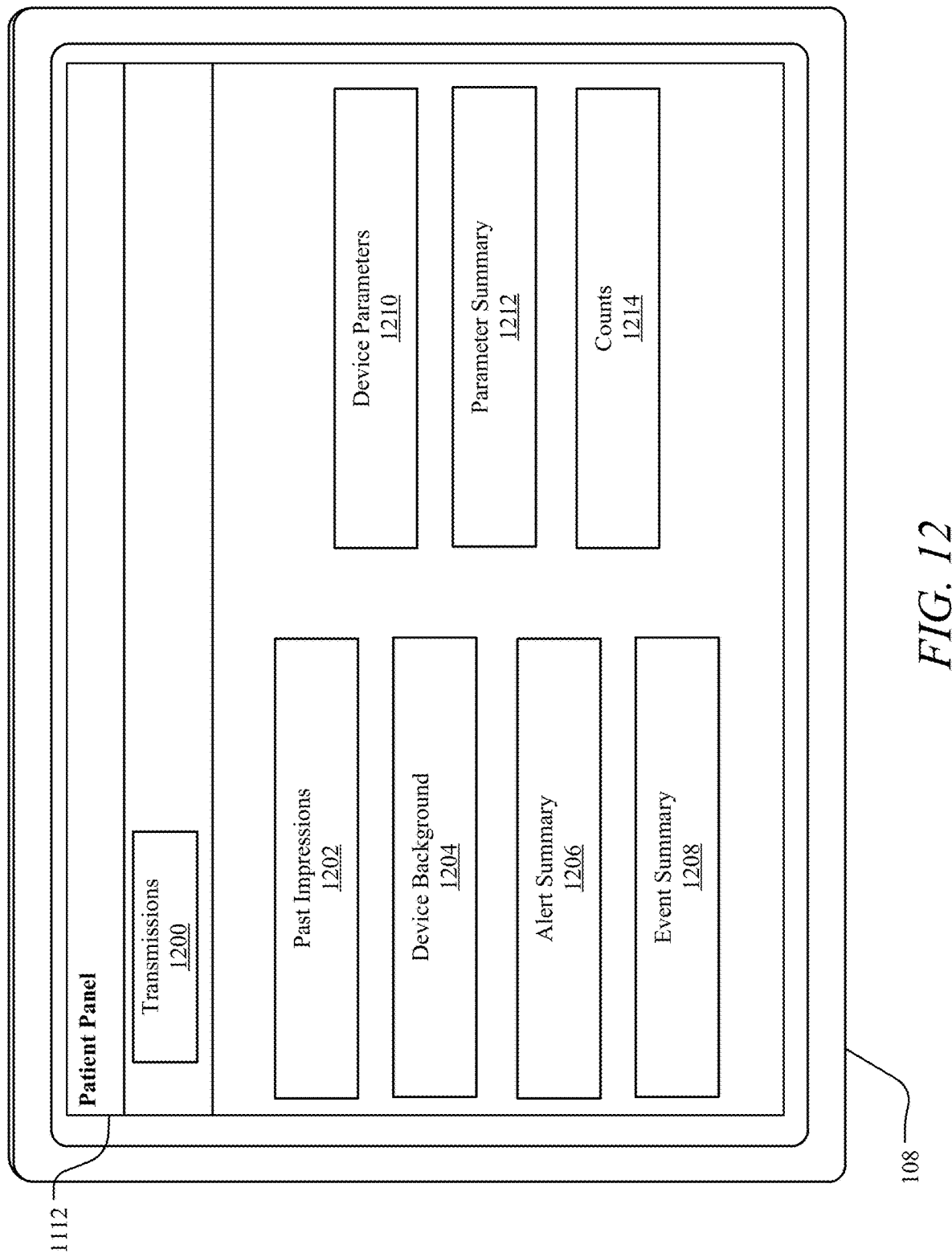
FIG. 12 shows an example patient panel user interface for managing patient medical devices.

Also included in the transmission overview interface 1100 is a patient panel 1112. FIG. 12 illustrates one example of a patient panel interface 1112. The patient panel interface 1112, similar to the above interface descriptions, may be displayed on a display portion of a user computing device 108. In general, the patient panel interface 1112 provides a universal tool for "at a glance" core data points for an effective and rapid diagnostic, impression, and plan for a defined reporting period of a patient based on received transmissions from the patient's medical device. Although particular portions and information are discussed below as being included in the patient panel 1112, more or fewer information portions may be included in the interface.

Near the top of the interface 1112, a transmissions 1200 portion is displayed. The transmissions portion 1200 includes general information about a selected patient and transmissions from a medical device associated with the patient. For example, the transmissions 1200 may include a date and type of a current transmission, date and type of past transmissions, an estimated battery life of the medical device based on received transmissions, and the like. In addition, the patient panel interface 1112 may include a past impressions portion 1202 that displays past clinical impressions related to the patient, the transmission, or any other category for rapid recapture of prior key events in patient/device interactions at the clinic. Algorithms may be executed by the medical device manager 102 to collate previously approved or created dockets for the patient/transmissions and apply every clinical impression or some clinical impressions for the patient. Links to transmissions associated with each displayed past impression may also be included in the past impressions portion 1202. In some implementations, similar past impressions may be collected and displayed in a single impression, with each individual impression available through a drop-down menu arranged by date of occurrence of the past impression.

Manufactures offer no historical structure for data transmissions. Instead, the transmissions are presented as list and purged over time, with each manufacturer managing past transmissions differently. The medical device manager 102 dates each transmission and stores it in perpetuity, enabling care providers to store and correlate past transmissions 1202 with docket reports. Thereafter dockets are approved, the past transmissions 1202 can be recalled within each historical docket. Key events are further pulled from each docket and displayed in the patient panel interface 1112 and clickable so that user can click that event and go straight to the relevant portion of a transmission and the associated docket that made the conclusion and care protocol decision.

Also included in the patient panel interface 1112 is a device background section 1204. The device background section 1204 may display core data of the device as it relates to the patient, including date of implant, device type, patient disease type, and any other device background information to aid the user of the interface 1112 in processing a received transmission from the medical device of the patient.

An alert summary portion 1206 may also be displayed in the patient panel interface 1112 that provides alerts associated with a particular transmission (such as a transmission indicated in the transmissions section 1200 at the top of the patient panel interface 1112). An event summary portion 1208 may also be provided for the particular transmission. In general, the alerts and events are scrubbed and normalized to remove items that are duplicates and to provide the received transmissions data in a format that the medical device manager 102 may process. An event in the event summary 1208 may therefore include an event type, date and time of occurrence, and duration of the event. An event in the event summary 1208 may be automatically associated with a docket through a selection by a user of the interface 1112. Once associated with a docket through the event summary portion 1208, the associated section of a .PDF report for the transmission with that event is linked for automated display for review by the user. The .PDF document event may also be automatically included in the device manager 102 docket. As events are received and reviewed by the user in the event summary 1208, the events may be archived and labeled as past events.

One or more parameters of a medical device of the patient may be displayed in a device parameters section 1210 and a summary of such parameters may be displayed in a parameter summary section 1212 of the patient panel interface 1112. In general, the device parameters 1210 and parameter summary 1212 are based on a particular medical device of a patient/transmission being displayed in the transmissions overview interface 1100. For example, an implanted cardiac device may include device parameters that include lead sensing voltages, lead impedance readings, and lead threshold information. Battery life and estimated time to replacement may also be determined and displayed. Regardless of the type of device associated with the parameters 1210 and summary 1212, data and/or other information may be transmitted from the device and received at the medical device manager 102. In many cases, such information may be provided in a particular format (e.g., HL7) that is then translated or normalized into a readable format by the medical device manager 102. In this manner, data received from various types of devices in various types of formats may be normalized and displayed in the device parameters 1210 and/or parameter summary 1212 for ease of understanding by the user of the interface 1112. Associated with the device information is a counts portion 1214 of the patient panel interface 1112 that displays or otherwise indicates one or more counts of device events received at the medical device manager 102.

Returning to the transmission overview interface 1100 of FIG. 11, a transmission manufacturer report 1114 is provided within the interface. In general, the transmission manufacturer report 1114 is displayed per selected transmission as delivered from a device's manufacturer servers. In particular, the medical device manager 102 may determine a particular manufacturer of a medical device transmitting information or data to the manager. In response, the manager 102 may access one or more servers associated with the manufacturer of the device to retrieve a corresponding manufacturer's report on the device. The report may include device operational details, such as test results and operational parameters of the device. The report may be displayed as a .PDF document along with the data received through the transmission from the device, all in one interface 1100.

In addition to the displayed report, the transmission manufacturer report 1114 section may include an interactive report list 1116 portion and an add to docket 1118 selector. The report list 1116 provides a mechanism through which the user may access other .PDF reports associated with a transmission. For example, a single transmission may be associated with several manufacturer reports. Each of reports may be accessible through the report list 1116. In one implementation, the report list 1116 may be a drop-down menu or other listing of the available reports for the transmission and selectable by a user of the interface 1100. In addition, the add to docket selector 1118 allows the user to click or otherwise select the selector to include the displayed .PDF report with a docket associated with the patient or transmission.

Figure 14:
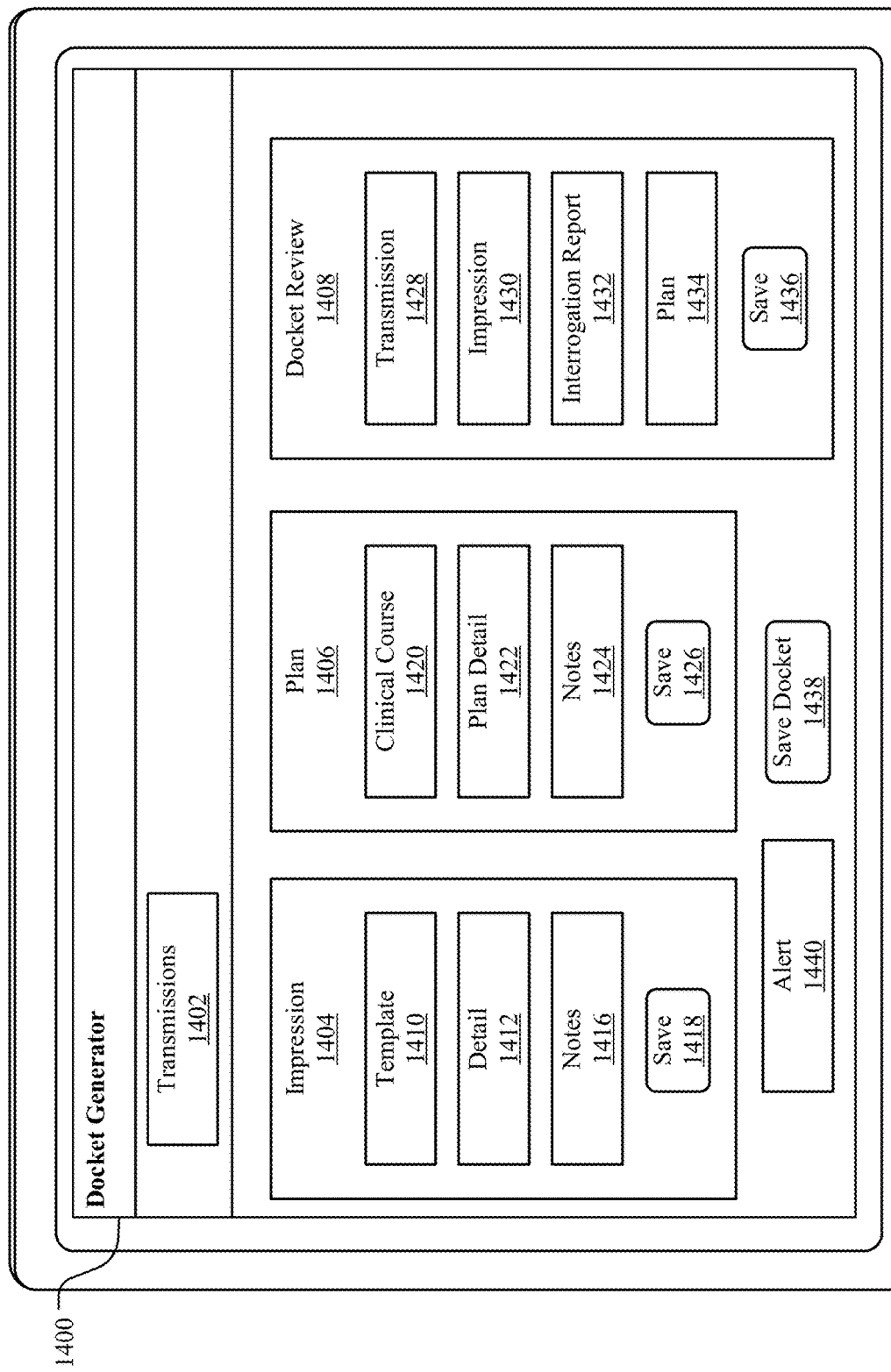
FIG. 14 shows an example docket generator user interface for managing patient medical devices.

The docket generator 1104 selector in the transmission overview interface 1100 allows a user to generate a docket for the transmission displayed in the interface. FIG. 14 illustrates an example docket generator user interface for managing patient medical devices. The docket generator interface 1400 may be displayed on the user's computing device 108 upon selection of the docket generator selector 1104 in the transmission overview interface 1100. Similar to other interfaces discussed above, the docket generator interface 1400 may include a transmissions 1402 indicator that provides context into which transmissions the docket is associated with. In addition, the user may utilize the docket generator interface 1400 to create and/or manage impressions 1404, plans 1406, and overall review 1408 of a docket associated with one or more transmissions from a medical device.

In the impression 1404 section of the docket generator, a user of the interface 1400 may add one or more impressions to a received transmission associated with the docket. In one implementation, the impression 1404 section may include one or more impression templates 1410 that are selectable by the user of the interface 1400. The impression templates may be constructed to reflect industry standard terminology as it relates to transmission diagnostics. Further portions of the impression 1404 generator may include details 1412 of the impression selectable through one or more interactive menus and a section for including notes 1416 of the impression. Any added impressions through the impression 1404 interface may be saved through activation of a save button 1418. Saved impressions may be automatically exported to relevant interfaces through the medical device manager 102. Further, information may be automatically imported into the docket based on the impressions 1404 selected by the user and such impressions may be editable.

In a similar manner, a plan section 1406 may be provided in the docket generator interface 1400. The plan portion may allow a user to select a clinical course 1420 for a patient in response to a received device transmission, including medical plan details 1422 and notes 1424 to associate with the plan. As above, the clinical course 1420 and/or plan details 1422 may be selectable from one or more menus or may accept editable text. A save button 1426 is provided within the plan section 1406 to save medical plans in the docket for the received transmission.

A docket review section 1408 may also be included in the interface 1400. The docket review section 1408 may include an overview of general transmission information 1428 for the particular docket, entered impressions 1430 for the docket, an entered medical plan 1434, and/or an interrogation report section 1432 through which manufacturer reports (perhaps in .PDF format) may be selected to include in the docket. In this section 1408, the user may review the information to be included in the created docket and approve of the docket. In the docket review section 1408 or in other locations (save docket button 1438), the user may select to save the docket in the medical device manager 102 system. In some implementations, multiple save options may be provided through save 1436 or save docket 1438, such as dockets to be saved for later that are awaiting a billable opportunity window or the like or dockets saved for clinic staff approval. In addition, the interface 1400 may include one or more alerts 1440 that indicate that a docket cannot be saved for any reason, including missing information, unexpected information, exceeding character limits in one or more fields, and the like.

In some implementations of the medical device manager 102, clearing of a transmission or patient in the system may be reduced to two clicks or inputs from the user of the interface, thereby increasing efficiency of a clinic by 95%. For example and returning FIG. 4, the user specific portal 400 includes a patient summary section 404. This portal is typically the first interface that a user would encounter upon accessing the medical device manager 102. In the patient portal 404 (illustrated in more detail in FIG. 8), patients with transmissions that are received at the medical device manager 102 is displayed, including a start button 820 for each patient/transmission. By selecting this start button 820 (one click), the interface is linked to the transmission overview interface 1100 of FIG. 11. Further, upon selection of the start button 820, a default docket may be generated from information obtained from the received transmission. In particular, a default impression and plan may be automatically populated into the default docket for commonly received transmissions. For example, transmissions with no alerts or events associated with the transmission may receive a default plan for no change in the patient care ("Routine Remote Transmission") and an impression ("No Device Check: Remote"). This information (impression and medical plan) may be auto-populated into a docket and presented to the user of the interface 1100 for approval. If approved, the user may simply click on a save docket button (click two) to save the docket for the transmission and save the docket for use by the system. In this manner, a default docket may be generated for particular transmissions and approved through two clicks or inputs from the user into the interface. Episodes that are sent with a non-event may be automatically removed, and the transmission is analyzed to determine if there are any transmissions remaining with any episodes. If the episode count is zero, the transmission is treated as normal device function (NDF) and the docket is automatically populated with corresponding NDF impressions and plan and colored green. Dockets may be saved for later awaiting a billable opportunity or window. Further, manufacturer report PDFs may be selected for inclusion in the docket enabled by multiple transmission management.

In one implementation, dockets are generated once the impression 920 has been selected. An impression is selected for at least one transmission in a docket. This includes auto generated impressions 920 for NDF. If events exist, an impression is based off of that event(s). These events come via HL7 in IDCO format and are normalized into industry standards by the medical device manager 102. Impressions 920 populate a smart phrase that is included in the docket. Once an impression 920 is selected the user can build the care plan 922. Impressions 920 are discrete data points and the user may select as many as deemed appropriate. To auto-populate the impression 920, the medical device manager 102 generates and utilizes a look-up editable data library of possible impression responses aligned with transmission data points. Many are default look-ups based on typical transmission data points-impression pairs. If a transmission has no events and is flagged as green, the medical device manager 102 generates a NDF impression 920. For that transmission, the impression 920 is auto selected and as a result the smart phrase is generated. NDF is identified where the transmission has no current events when it is received. The impression 920 is auto attached to the docket removing the impression 920 from the docket. The user is able to generate a docket as a second click since the impression 920 has already been attached. The care plan 922 is auto generated for NDF when the transmission has no events and has the auto generated the impression 920 as NDF. Where there are events, the medical device manager 102 prompts the user to make an impression 920 from the drop down reflecting the full relevant data from the look-up table. The impression 920 is selected from a dropdown and has a numerical value associated with the look up table. This value represents a smart phrase impression in the database. Dropdown impression selection 920 is based on device type and/or data field transmitted.

Figure 15:
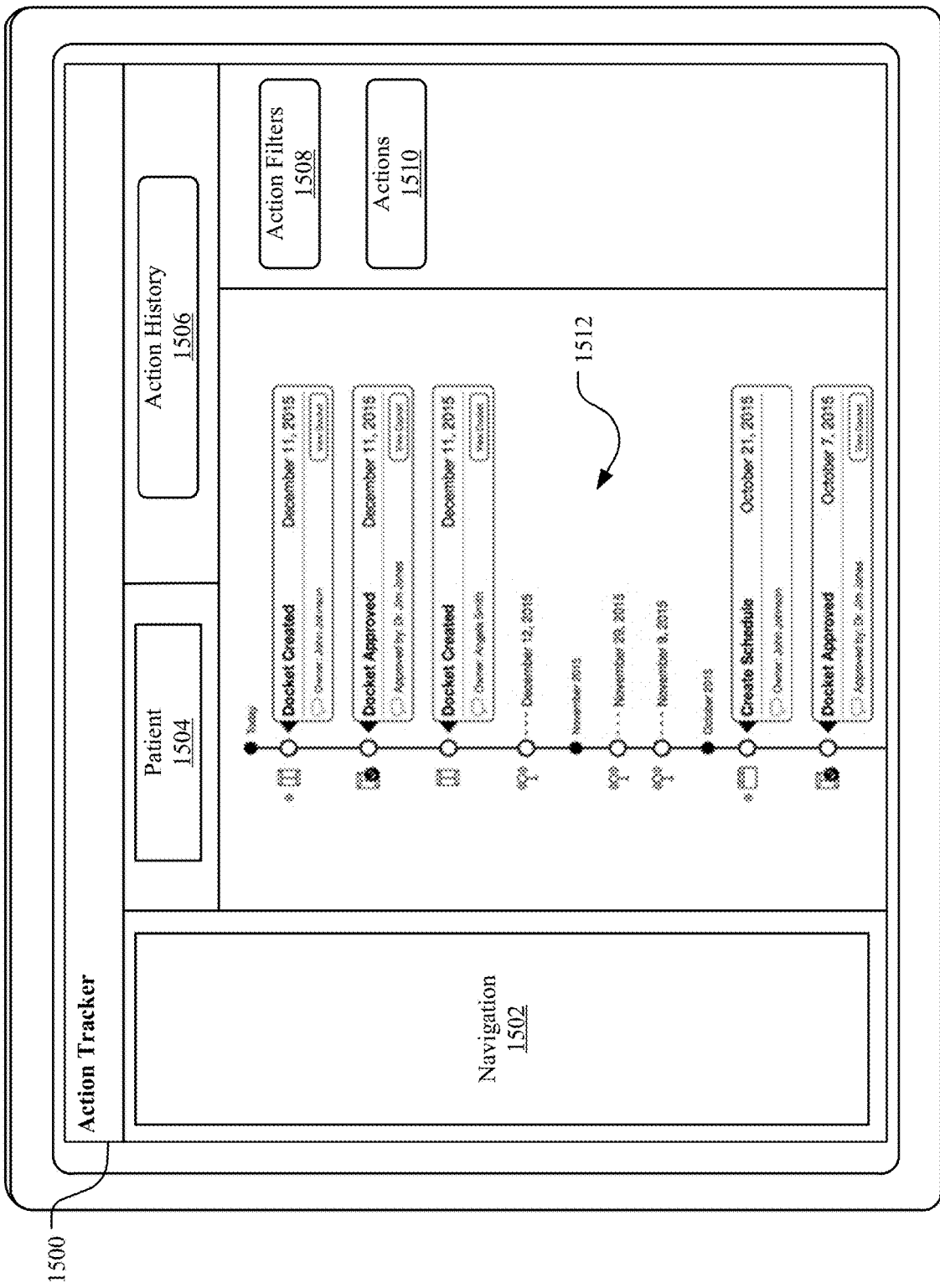
FIG. 15 shows an example action tracker user interface for managing patient medical devices.

FIG. 15 shows an example action tracker user interface 1500 for managing patient medical devices. Like the other interfaces discussed herein, the action tracker 1500 may be managed and provided by the medical device manager 102 and displayed on a user computing device 108 upon logging into the manager. In general, the action tracker 1500 provides an audit tracking feature to the user of a detailed historical view of all actions taken with respect to a CIED, including transmissions, patient information, and dockets. Although portions of the interface 1500 are discussed below, it should be appreciated that more or fewer portions may be included in the interface.

In some implementations, the action tracker interface 1500 includes a navigation portion 1502. The navigation portion 1502 includes links or other selectable portions that allow a user to access other interfaces of the medical device manager 102, such as those interfaces discussed herein. Patient information 1504 for the action tracker 1500 may be entered and displayed in another portion of the interface. The user may utilize the action history selector 1506 to request and view the action tracking for the patient identified in the patient information portion 1504. Once selected, a timeline of actions 1512 undertaken and tracked by the medical device manager 102 is displayed in the interface 1500. In general, the timeline of actions 1512 is a summary of all actions undertaken by the system for the device or patient identified. For example, the timeline 1512 may include an entry for docket creation, medical plan creation, transmissions received, dockets approved, etc. Each entry in the timeline 1512 may or may not include dates associated with each entry for easy understanding by the user.

Further, the timeline of action 1512 may be editable or configurable by the user of the interface 1500. For example, one or more drop down menus for selecting action filters 1508 may be provided to configure the type and number of actions included in the timeline 1512. Particular actions 1510 may be selected or deselected to be included in or removed from the timeline 1512, respectively. Through the selection of action filters 1508 and/or specific actions 1510, the user may configure the timeline 1512 in a manner that is most efficient and useful to the user.

Figure 16:
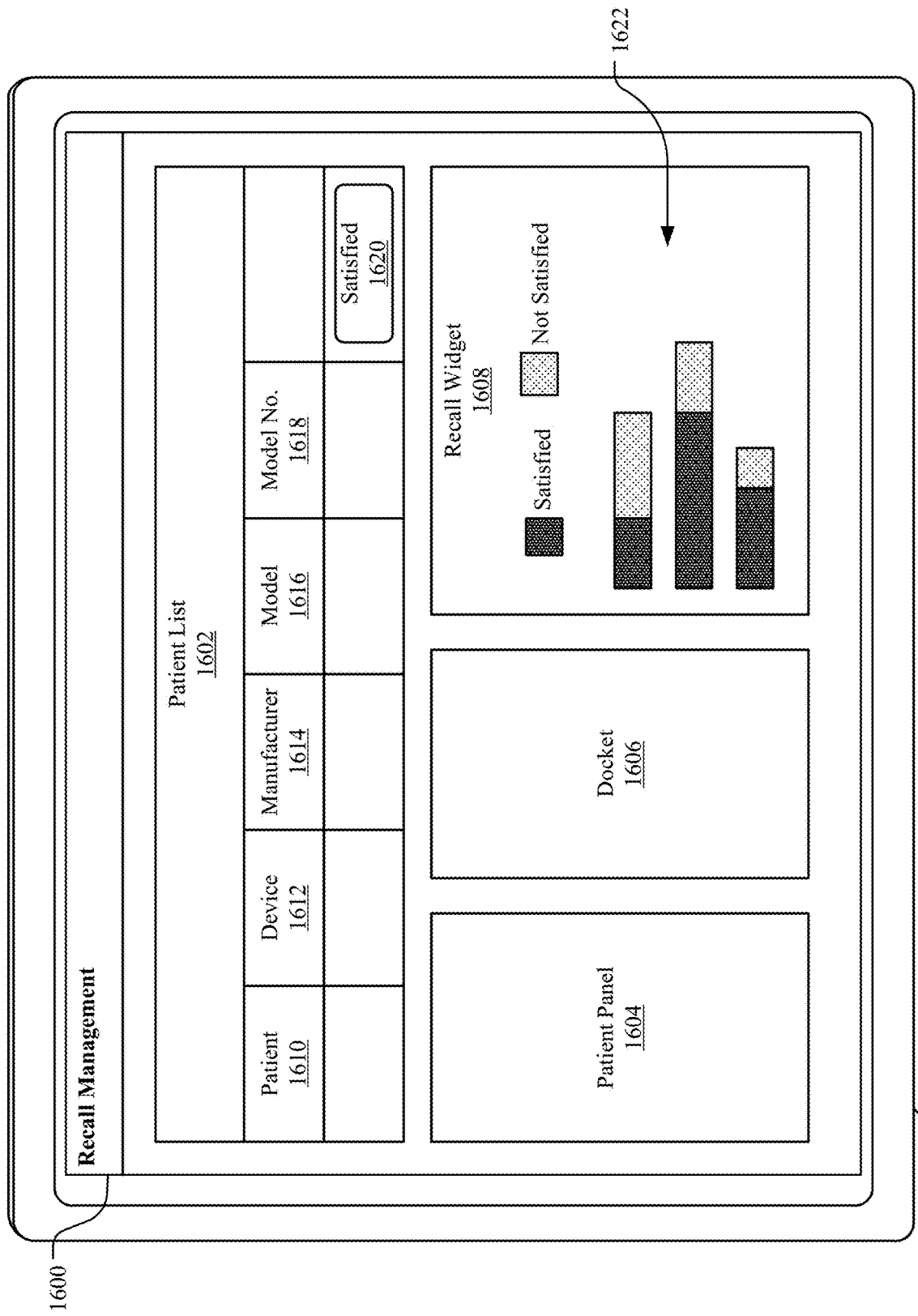
FIG. 16 shows an example recall management user interface for managing patient medical devices.
Figure 17:
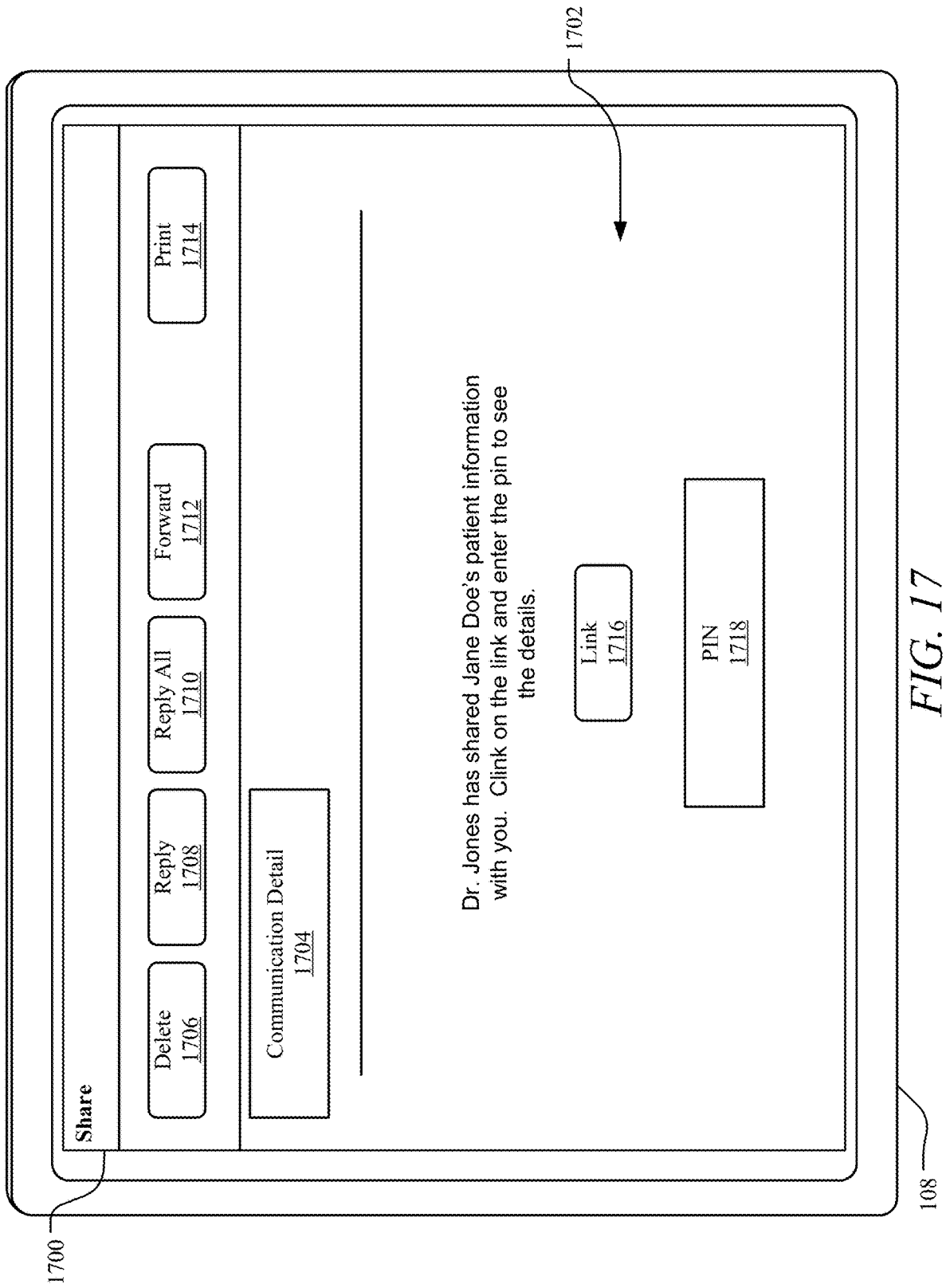
FIG. 17 shows an example information sharing user interface for managing patient medical devices.

FIG. 16 shows an example recall management user interface 1600 for managing patient medical devices. The recall management interface 1600 automatically identifies a recalled/advisory device and the patients associated with that device. For example, recall data may be gathered from a variety of public and private sources and imported into the medical device manager 102. Once a recall or advisory notice is verified with a manufacturer, the medical device manager 102 may determine which patients in a database are associated with the device and provide an indication of such patients in the recall management interface 1600. Once the patients are identified through the recall management interface 1600, a notice or some other type of alert may be generated to inform the patients and/or clinic staff of the recall/advisory of the device and a medical plan may be formulated for the patient accordingly.

In one implementation, the recall management interface 1600 includes a listing 1602 of patients identified as having the recalled/advisory medical device. Each patient entry in the patient list 1602 may include a patient name 1610, a type of medical device 1612, a manufacturer of the device 1614, a model type of the device 1616, and a model number 1618. This information may be utilized by the user to verify that the patient is associated with the recalled device. Further, each entry in the patient list 1602 may include a satisfied button 1620 that the user may select once an action has been taken concerning the recall for the patient identified. In other words, once a notice, alert, or medical plan has been implemented and completed, the user of the interface 1600 may select the satisfied button 1620 for the patient. In one implementation, selection of the satisfied button 1620 may remove the corresponding patient from the patient list.

A recall widget 1608 may also be included that provides statistics and information on identified recalls/advisories. The recall widget 1608 may include a number and/or graph for each received recall/advisory and the number of satisfied and not satisfied patients for the clinic. In addition, a patient portal section 1604 may be included that is populated with patient information upon being selected from the patient list 1602 and a corresponding docket 1606 for the selected patient may be presented. Through the recall management interface 1600, therefore, one or more device recalls and/or advisories may be processed for patients of the clinic. Recalls and the status of individual processes for recalls may also be included in other interfaces, including but not limited to the user specific docket interface 900 discussed above.

The medical device manager 102 may also allow users to share documents with other entities. In particular, such third party entities may be HIPAA qualified to receive patient information, such as doctors, cardiologists, nurses, primary care doctors, etc.). Through a share interface 1700 illustrated in FIG. 17, a user of the medical device manager 102 may share/receive patient-related document, such as patient workflow or docket. To share information or a document, the user of the interface 1700 selects an option to share and a secure email is generated that includes the shared document. The email may include various options for managing the secure email, including delete 1706, reply 1708, reply all 1710, forward 1712, and print 1714, all which may be selected by the user. A communication detail 1704, such as a recipients email address, a sender address, a subject line, etc. may also be included.

The secure email, and more particularly the medical device manager 102, may communicate with the intended receiver of the document to verify that the receiver is HIPAA qualified. Once verified, the user will have access to the specific patient information being shared. The secure email may thus include a link 1716 to access the shared information and a PIN 1718 that the receiver enters to verify the receiver is the intended receiver. Upon entering of the PIN and selection of the link, the third party entity may have access to the document being shared and a notification confirming the sharing may be sent.

Figure 18:
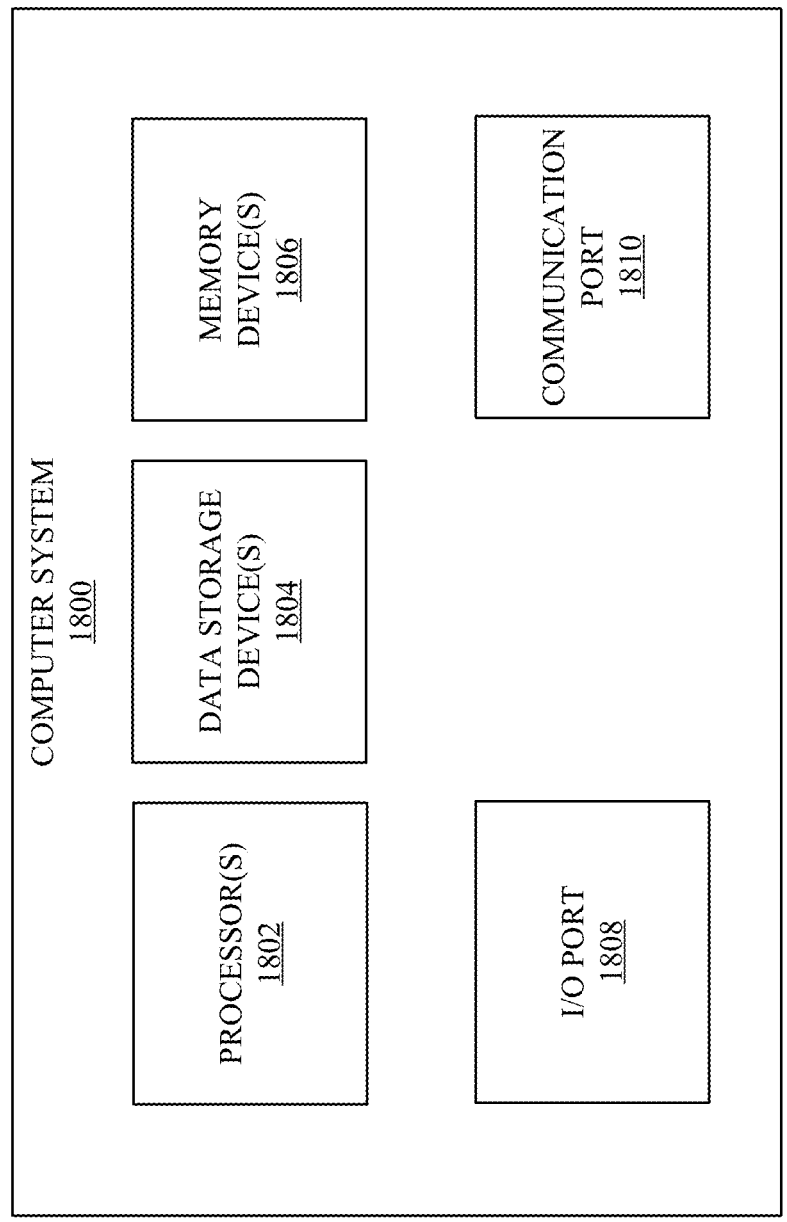
FIG. 18 is an example computing system that may implement various systems and methods discussed herein.

Referring to FIG. 18, a detailed description of an example computing system 1800 having one or more computing units that may implement various systems and methods discussed herein is provided. The computing system 1800 may be applicable to the medical device manager 102 and/or the user computing device 108 and other computing or network devices. It will be appreciated that specific implementations of these devices may be of differing possible specific computing architectures not all of which are specifically discussed herein but will be understood by those of ordinary skill in the art.

The computer system 1800 may be a computing system is capable of executing a computer program product to execute a computer process. Data and program files may be input to the computer system 1800, which reads the files and executes the programs therein. Some of the elements of the computer system 1800 are shown in FIG. 18, including one or more hardware processors 1802, one or more data storage devices 1804, one or more memory devices 1808, and/or one or more ports 1808-1810. Additionally, other elements that will be recognized by those skilled in the art may be included in the computing system 1800 but are not explicitly depicted in FIG. 18 or discussed further herein. Various elements of the computer system 1800 may communicate with one another by way of one or more communication buses, point-to-point communication paths, or other communication means not explicitly depicted in FIG. 18.

The processor 1802 may include, for example, a central processing unit (CPU), a microprocessor, a microcontroller, a digital signal processor (DSP), and/or one or more internal levels of cache. There may be one or more processors 1802, such that the processor 1802 comprises a single central-processing unit, or a plurality of processing units capable of executing instructions and performing operations in parallel with each other, commonly referred to as a parallel processing environment.

The computer system 1800 may be a conventional computer, a distributed computer, or any other type of computer, such as one or more external computers made available via a cloud computing architecture. The presently described technology is optionally implemented in software stored on the data stored device(s) 1804, stored on the memory device(s) 1806, and/or communicated via one or more of the ports 1808-1810, thereby transforming the computer system 1800 in FIG. 18 to a special purpose machine for implementing the operations described herein. Examples of the computer system 1800 include personal computers, terminals, workstations, mobile phones, tablets, laptops, personal computers, multimedia consoles, gaming consoles, set top boxes, and the like.

The one or more data storage devices 1804 may include any non-volatile data storage device capable of storing data generated or employed within the computing system 1800, such as computer executable instructions for performing a computer process, which may include instructions of both application programs and an operating system (OS) that manages the various components of the computing system 1800. The data storage devices 1804 may include, without limitation, magnetic disk drives, optical disk drives, solid state drives (SSDs), flash drives, and the like. The data storage devices 1804 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1806 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1804 and/or the memory devices 1806, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1800 includes one or more ports, such as an input/output (I/O) port 1808 and a communication port 1810, for communicating with other computing, network, or vehicle devices. It will be appreciated that the ports 1808-1810 may be combined or separate and that more or fewer ports may be included in the computer system 1800.

The I/O port 1808 may be connected to an I/O device, or other device, by which information is input to or output from the computing system 1800. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1800 via the I/O port 1808. Similarly, the output devices may convert electrical signals received from computing system 1800 via the I/O port 1808 into signals that may be sensed as output by a human, such as sound, light, and/or touch. The input device may be an alphanumeric input device, including alphanumeric and other keys for communicating information and/or command selections to the processor 1802 via the I/O port 1808. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 1800 via the I/O port 1808. For example, an electrical signal generated within the computing system 1800 may be converted to another type of signal, and/or vice-versa. In one implementation, the environment transducer devices sense characteristics or aspects of an environment local to or remote from the computing device 1800, such as, light, sound, temperature, pressure, magnetic field, electric field, chemical properties, physical movement, orientation, acceleration, gravity, and/or the like. Further, the environment transducer devices may generate signals to impose some effect on the environment either local to or remote from the example computing device 1800, such as, physical movement of some object (e.g., a mechanical actuator), heating or cooling of a substance, adding a chemical substance, and/or the like.

In one implementation, a communication port 1810 is connected to a network by way of which the computer system 1800 may receive network data useful in executing the methods and systems set out herein as well as transmitting information and network configuration changes determined thereby. Stated differently, the communication port 1810 connects the computer system 1800 to one or more communication interface devices configured to transmit and/or receive information between the computing system 1800 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1810 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1810 may communicate with an antenna or other link for electromagnetic signal transmission and/or reception.

The system set forth in FIG. 18 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined in blocks differently in various implementations of the disclosure or described with different terminology. These and other variations, modifications, additions, and improvements may fall within the scope of the disclosure as defined in the claims that follow.

What is claimed is:

1. A method for patient device management, the method comprising:

receiving, using a wireless transmission interface, interrogation data originating from a cardiac implantable electronic device corresponding to an interrogation for a patient, the interrogation data including device data for the cardiac implantable electronic device and patient specific data for the patient, the cardiac implantable electronic device being manufactured by one of a plurality of manufacturers;

generating, using one or more processors of a computing device, manufacturer independent interrogation data by normalizing the interrogation data of the plurality of manufacturers through a conversion of the interrogation data into a unified format;

parsing, using the one or more processors of the computing device, the manufacturer independent interrogation data to determine at least one key identifier associated with the cardiac implantable electronic device or the patient;

associating, using the one or more processors of the computing device, the manufacturer independent interrogation data with at least one permitted user;

extracting, using the one or more processors of the computing device, discrete data based on data mapping of the manufacturer independent interrogation data;

generating, using the one or more processors of the computing device and based on the extracted discrete data, provider-oriented information for the interrogation, the provider-oriented information including an association of the at least one key identifier and the manufacturer independent interrogation data;

assigning, using the one or more processors of the computing device, a processing state to the interrogation using the provider-oriented information;

aggregating, using the one or more processors of the computing device, the interrogation into a category based on the processing state, the category associated with an action by the at least one permitted user, the category being:
  backlog when the processing state is passive,
  compose when the processing state is saved, and
  hidden when the processing state is archived; and presenting the provider-oriented information according to the category using at least one display communicatively coupled to the computing device, wherein presenting the provider-oriented information comprises a two-click approval including:
  displaying a start button corresponding to the interrogation;
  upon a selection of the start button, generating a docket including an automatically generated impression and an automatically generated care plan;
  displaying a save button corresponding to the docket; and
  upon a selection of the save button, saving the docket,
wherein the category is cleared following the two-click approval by the at least one permitted user.

2. The method of claim 1, wherein the processing state is docketed.

3. The method of claim 2, wherein the category is needs approval when the processing state is docketed.

4. The method of claim 1, wherein the at least one permitted user is at least one of: a professional associated with a clinic or a third party to which access rights were delegated.

5. The method of claim 1, wherein the interrogation data is received from memory and obtained from the cardiac implantable electronic device using a manufacturer-specific programmer during an in-office visit.

6. The method of claim 5, wherein a data file for the interrogation is generated by the manufacturer-specific programmer and normalizing the interrogation data includes parsing the data file into a parsed data file using a plurality of parsing stages.

7. The method of claim 1, wherein the interrogation is a remote interrogation and the interrogation data is received over a network from a manufacturer system using a Health Level 7 (HL7) communication protocol and an Implantable Device Cardiac Observation (IDCO) data standard.

8. The method of claim 7, wherein normalizing the interrogation data includes HL7 data extraction by mapping unidentified HL7 data to one or more interrogation fields and normalizing IDCO data.

9. The method of claim 8, wherein normalizing the interrogation data further includes device setting calculations and normalization.

10. The method of claim 1, wherein the interrogation is assigned a severity based on an association of the interrogation with an event type.

11. The method of claim 10, wherein the severity is a normal device function where the event type is no event.

12. The method of claim 11, a prompt for the two-click approval generated in response to the severity being assigned the normal device function.

13. The method of claim 12, wherein the prompt includes the automatically generated impression and the automatically generated care plan corresponding to the normal device function.

14. The method of claim 1, further comprising:
  generating one or more billing opportunities for a clinic based on the category.

15. The method of claim 14, wherein the one or more billing opportunities are determined based on a reimbursement rate, a frequency of available reimbursements, and a number of patients.

16. The method of claim 14, wherein the one or more billing opportunities includes determining a billing window corresponding to the interrogation based on a number of days since the interrogation and a minimum and a maximum number of days between billable events.

17. The method of claim 1, further comprising:
  generating an audit trail for the cardiac implantable electronic device, the audit trail including at least one of past interrogations, the interrogation, or action taken with respect to the cardiac implantable electronic device.

18. The method of claim 1, further comprising:
  generating community analytics for a clinic based on the category, the community analytics including a comparison of the clinic to at least one of a second clinic or a benchmark for a plurality of clinics.

19. The method of claim 1, wherein the computing device is configured to generate interrogation report form the manufacturer independent interrogation data, the interrogation report is included in a stack of interrogation reports for the cardiac implantable electronic device, each in the stack of interrogation reports corresponding to a disparate interrogation.

20. A method for patient device management, the method comprising:
  establishing a wireless network connection between a computing device and a cardiac implantable electronic device;
  receiving, using the wireless network connection, interrogation data originating from the cardiac implantable electronic device corresponding to an interrogation for a patient, the interrogation data including device data for the cardiac implantable electronic device and patient specific data for the patient, the cardiac implantable electronic device being manufactured by one of a plurality of manufacturers;
  generating, using one or more processors of the computing device, manufacturer independent interrogation data by normalizing the interrogation data of the plurality of manufacturers through a conversion of the interrogation data into a unified format;
  parsing, in a first stage, using the one or more processors of the computing device, the manufacturer independent interrogation data to determine at least one key identifier associated with the cardiac implantable electronic device or the patient;
  associating, using the one or more processors of the computing device, the manufacturer independent interrogation data with at least one permitted user;

parsing, in a second stage, using the one or more processors of the computing device, the manufacturer independent interrogation data, to extract discrete data using data mapping;

generating, using the one or more processors of the computing device and based on the extracted discrete data, provider-oriented information for the interrogation, the provider-oriented information including an association of the at least one key identifier and the manufacturer independent interrogation data;

assigning, using the one or more processors of the computing device, a processing state to the interrogation using the provider-oriented information, the processing state being passive, saved, or archived;

aggregating, using the one or more processors of the computing device, the interrogation into a category based on the processing state, the category associated with an action by the at least one permitted user, the category being:

backlog when the processing state is passive,
compose when the processing state is saved, and
hidden when the processing state is archived; and presenting the provider-oriented information according to the category using at least one display communicatively coupled to the computing device, wherein presenting the provider-oriented information comprises a two-click approval including:

displaying a start button corresponding to the interrogation;

upon a selection of the start button, generating a docket including an automatically generated impression and an automatically generated care plan;

displaying a save button corresponding to the docket; and upon a selection of the save button, saving the docket, wherein the category is cleared following the two-click approval by the at least one permitted user.

* * * * *